US008252875B2

(12) United States Patent
Mihan et al.

(10) Patent No.: US 8,252,875 B2
(45) Date of Patent: Aug. 28, 2012

(54) PROCESS FOR THE PREPARATION OF UNSYMMETRIC BIS(IMINO) COMPOUNDS

(75) Inventors: Shahram Mihan, Bad Soden (DE); Benno Bildstein, Innsbruck (AT); Lars Kölling, Mannheim (DE); Alexander Solchinger, Buers (AT); Sascha Schlawjinski, Mörfelden-Walldorf (DE)

(73) Assignee: Basell Polyolefine GmbH, Wesseling (DE)

( * ) Notice: Subject to any disclaimer, the term of this patent is extended or adjusted under 35 U.S.C. 154(b) by 470 days.

(21) Appl. No.: 12/087,554

(22) PCT Filed: Jan. 8, 2007

(86) PCT No.: PCT/EP2007/000096
§ 371 (c)(1),
(2), (4) Date: Jul. 9, 2008

(87) PCT Pub. No.: WO2007/080081
PCT Pub. Date: Jul. 19, 2007

(65) Prior Publication Data
US 2009/0054609 A1   Feb. 26, 2009

Related U.S. Application Data

(60) Provisional application No. 60/811,013, filed on Jun. 5, 2006.

(30) Foreign Application Priority Data

Jan. 13, 2006 (DE) .................. 10 2006 001 959

(51) Int. Cl.
C08F 4/80 (2006.01)
C08F 4/70 (2006.01)
C08F 4/60 (2006.01)
C07F 15/02 (2006.01)
B01J 31/28 (2006.01)

(52) U.S. Cl. ............. 526/172; 526/161; 526/169.1; 526/169; 526/904; 502/103; 556/138

(58) Field of Classification Search .............. 556/138; 526/169.1, 172, 161
See application file for complete search history.

(56) References Cited

U.S. PATENT DOCUMENTS

| 3,125,547 | A | 3/1964 | Blatz |
| 3,242,150 | A | 3/1966 | Scoggin |
| 3,248,179 | A | 4/1966 | Norwood |
| 4,438,238 | A | 3/1984 | Fukushima et al. |
| 4,461,873 | A | 7/1984 | Bailey et al. |
| 5,153,157 | A | 10/1992 | Hlatky |
| 5,306,775 | A | 4/1994 | Martin et al. |
| 5,319,029 | A | 6/1994 | Martin et al. |
| 5,324,800 | A | 6/1994 | Welborn, Jr. |
| 5,350,807 | A | 9/1994 | Pettijohn |
| 5,372,980 | A | 12/1994 | Davis et al. |
| 5,380,803 | A | 1/1995 | Coutant et al. |
| 5,382,630 | A | 1/1995 | Stehling et al. |
| 5,530,065 | A | 6/1996 | Farley et al. |
| 5,539,076 | A | 7/1996 | Nowlin et al. |
| 5,565,534 | A | 10/1996 | Aulbach |
| 5,633,394 | A | 5/1997 | Welborn |
| 5,698,642 | A | 12/1997 | Govoni et al. |
| 5,703,187 | A | 12/1997 | Timmers et al. |
| 5,707,751 | A | 1/1998 | Garza et al. |
| 5,710,297 | A | 1/1998 | Weller et al. |
| 5,770,753 | A | 6/1998 | Kuber et al. |
| 5,786,432 | A | 7/1998 | Kuber et al. |
| 5,840,644 | A | 11/1998 | Kuber et al. |
| 5,840,948 | A | 11/1998 | Rohrmann et al. |
| 5,852,142 | A | 12/1998 | Rohrmann et al. |
| 5,852,145 | A | 12/1998 | McLain |
| 5,929,264 | A | 7/1999 | Rohrmann et al. |
| 5,955,555 | A | 9/1999 | Bennett |
| 5,990,254 | A | 11/1999 | Weller et al. |
| 6,002,034 | A | 12/1999 | McLain et al. |
| 6,051,522 | A | 4/2000 | Rohrmann et al. |
| 6,051,727 | A | 4/2000 | Kuber et al. |
| 6,087,291 | A | 7/2000 | Speca |
| 6,160,145 | A | 12/2000 | Wu |
| 6,242,544 | B1 | 6/2001 | Kuber et al. |
| 6,255,506 | B1 | 7/2001 | Kuber et al. |
| 6,365,779 | B2 | 4/2002 | Devore et al. |
| 6,413,477 | B1 | 7/2002 | Govoni et al. |
| 6,417,302 | B1 | 7/2002 | Bohnen |
| 6,417,364 | B1 | 7/2002 | Lenges |
| 6,423,848 | B2 | 7/2002 | Bennett |
| 6,432,862 | B1 | 8/2002 | Bennett |
| 6,433,111 | B1 | 8/2002 | Kristen et al. |
| 6,444,606 | B1 | 9/2002 | Bingel et al. |
| 6,451,939 | B1 | 9/2002 | Britovsek |
| 6,455,660 | B1 | 9/2002 | Clutton et al. |

(Continued)

FOREIGN PATENT DOCUMENTS

CN   1850339   10/2006

(Continued)

OTHER PUBLICATIONS

Chen et al., Organometallics, 2003, 22, 4312-4321.*
Souane et al., C. R. Chemie, 2002, 5, 43-48.*
Estruelas et al., Organometallics, 2003, 22, 395-406.*
Small et al., "Highly Active Iron and Cobalt Catalysts For The Polymerization Of Ethylene", J. Am. Chem. Soc. 120, 1998, 4049-4050.
Britovsek et al., "Novel Olefin Polymerization Catalysts Based On Iron and Cobalt", J. Chem. Soc., Chem. Commun., 1998, p. 849.
Falbe et al., Römpp Chemie Lexikon, [Römpp Chemical Dictionary]; 9th ed; Thieme; 1992 New York; vol. 6 p. 5128-5129.
Lutz et al., "Pyridine Bis(imine) Or Iron Complexes For Ethylene and 1-Hexene (co)Polymerization", C.R. Chimie 5 (2002), pp. 43-48.

(Continued)

Primary Examiner — Rip A. Lee
(74) Attorney, Agent, or Firm — Dilworth IP LLC

(57) ABSTRACT

Process for the preparation of monoimine compounds, wherein a dicarbonyl compound is reacted in an aliphatic, non-aromatic solvent with aniline. Monoimine compounds having electron-withdrawing substituents in the ortho position and unsymmetric bis(imino) compounds and unsymmetric iron complexes prepared therefrom and the use thereof in the polymerization of olefins.

10 Claims, No Drawings

U.S. PATENT DOCUMENTS

| | | | |
|---|---|---|---|
| 6,465,386 | B1 | 10/2002 | Maddox et al. |
| 6,548,442 | B1 | 4/2003 | McDaniel et al. |
| 6,589,905 | B1 | 7/2003 | Fischer |
| 6,620,953 | B1 | 9/2003 | Bingel et al. |
| 6,645,901 | B2 | 11/2003 | Goto et al. |
| 6,657,026 | B1 | 12/2003 | Kimberley et al. |
| 6,683,141 | B1 | 1/2004 | Gibson et al. |
| 6,683,187 | B2 | 1/2004 | De Boer |
| 6,812,182 | B2 | 11/2004 | Wu et al. |
| 6,812,185 | B2 | 11/2004 | Fischer et al. |
| 6,878,785 | B2 | 4/2005 | McDaniel |
| 6,884,857 | B1 | 4/2005 | Stevens |
| 6,900,153 | B2 | 5/2005 | Preichuber-Pfuegl et al. |
| 7,038,070 | B2 | 5/2006 | Bingel |
| 7,053,160 | B1 | 5/2006 | Bingel et al. |
| 7,163,907 | B1 | 1/2007 | Canich |
| 7,666,959 | B2 | 2/2010 | Razavi |
| 7,723,448 | B2 | 5/2010 | Mihan et al. |
| 7,767,613 | B2 | 8/2010 | Mihan |
| 7,795,411 | B2 * | 9/2010 | Scholler et al. ............... 536/23.4 |
| 7,834,112 | B2 * | 11/2010 | Mihan et al. .................. 526/161 |
| 2001/0000519 | A1 | 4/2001 | Bennett |
| 2002/0061264 | A1 | 5/2002 | Govoni et al. |
| 2002/0072578 | A1 | 6/2002 | Wu et al. |
| 2002/0128403 | A1 | 9/2002 | Stevens et al. |
| 2003/0125195 | A1 | 7/2003 | Britovsek et al. |
| 2003/0171511 | A1 | 9/2003 | McDaniel et al. |
| 2004/0054088 | A1 | 3/2004 | Kazakov et al. |
| 2007/0066772 | A1 | 3/2007 | Foettinger et al. |
| 2007/0213205 | A1 | 9/2007 | Mihan et al. |
| 2007/0282110 | A1 | 12/2007 | Kolling |
| 2009/0054609 | A1 | 2/2009 | Mihan et al. |
| 2010/0087607 | A1 | 4/2010 | Mihan et al. |
| 2010/0093956 | A1 | 4/2010 | Mihan et al. |
| 2010/0234548 | A1 | 9/2010 | Kolling et al. |
| 2011/0281722 | A1 | 11/2011 | Kipke et al. |

FOREIGN PATENT DOCUMENTS

| | | |
|---|---|---|
| EM | 0545304 | 6/1993 |
| EP | 0100843 | 2/1984 |
| EP | 0129368 | 12/1984 |
| EP | 0416815 | 3/1991 |
| EP | 0533154 | 3/1993 |
| EP | 0533155 | 3/1993 |
| EP | 0533156 | 3/1993 |
| EP | 0533160 | 3/1993 |
| EP | 0561479 | 9/1993 |
| EP | 0576970 | 1/1994 |
| EP | 0632063 | 1/1995 |
| EP | 0659758 | 6/1995 |
| EP | 0661300 | 7/1995 |
| VU | WO-00/31090 | 6/2000 |
| WO | WO 91/09882 | 7/1991 |
| WO | WO-91/09882 | 7/1991 |
| WO | WO-95/11264 | 4/1995 |
| WO | WO-95/27005 | 10/1995 |
| WO | WO-96/00243 | 1/1996 |
| WO | WO-97/04015 | 2/1997 |
| WO | WO-97/36937 | 10/1997 |
| WO | WO-98/27124 | 6/1998 |
| WO | WO-98/40419 | 9/1998 |
| WO | WO-99/06414 | 2/1999 |
| WO | WO-9912981 | 3/1999 |
| WO | WO-99/46302 | 9/1999 |
| WO | WO-99/50318 | 10/1999 |
| WO | WO-00/05277 | 2/2000 |
| WO | WO-00/24787 | 5/2000 |
| WO | WO-00/58320 | 10/2000 |
| WO | WO-00/68279 | 11/2000 |
| WO | WO-01/25328 | 4/2001 |
| WO | WO-01/41920 | 6/2001 |
| WO | WO-01/58874 | 8/2001 |
| WO | WO 01/58874 A1 * | 8/2001 |
| WO | WO-02/28805 | 4/2002 |
| WO | WO 02/28805 A1 * | 4/2002 |
| WO | WO 02/28805 A2 * | 4/2002 |
| WO | WO 03/025028 A1 * | 3/2003 |
| WO | WO-2004/018489 | 3/2004 |
| WO | WO 2004/018489 A1 * | 3/2004 |
| WO | WO 2004/037415 A2 * | 5/2004 |
| WO | WO-2004/074333 | 9/2004 |
| WO | WO-2005/090371 | 9/2005 |
| WO | WO 2005/090371 A1 * | 9/2005 |

OTHER PUBLICATIONS

Strauss, "The Search for Larger and More Weakly Coordinating Anions", *Chem. Rev.* 93, 1993, pp. 927-942.

Esteruelas, et al., "Preparation, Structure, and Ethylene Polymerization Behavior of Bis(imino)pyridyl Chromium(III) Complexes", Organometallics, ACS, Washington, DC vol. 22, (2003), pp. 395-406.

Pelascini, et al., "Pyridine Bis(imino) Iron and Cobalt Complexes for Ethylene Polymerization: Influence of the Aryl Imino Substituents", *European Polymer Journal* 41 (2005) 1288-1295.

Chen et al., "Halogen-Substituted 2,6-Bis(imino)Pyridyl Iron and Cobalt Complexes: Highly Active Catalysts for Polymerization and Oligomerization of Ethylene", *Organometallics*, ACS, Washington, DC, vol. 22, (2003) pp. 4312-4321.

Thabet, et al., "2,2'-[2,6-Pyridinediylbis(methylidynenitrilo)]diphenol: A Highly Selective Reagent for the Detection of U(VI), Sb(III), and Bi(III)", *Analytical Chemistry*, vol. 47, No. 11, Sep. 1975.

Scott, et al., "Multiple Pathways for Dinitrogen Activation during the Reduction of an Fe Bis(iminepyridine) Complex", Inorganic Chemistry vol. 47 No. 3 2008 , 896-911.

Vidyaratne, et al., "Reactivity of Chromium Complexes of a Bis(imino)pyridine Ligand: Highly Active Ethylene Polymerization Catalysts Carrying the Metal in a Formally Low Oxidation State", Organometallics 26 2007 , 3201-3211.

Bouwkamp, et al., "Bis(imino)pyridine Ligand Deprotonation Promoted by a Transient Iron Amide", Inorganic Chemistry vol. 45 No. 1 2006 , 2-4.

Sun, Wen-Hua et al., "Iron Complexes Bearing 2-Imino-1,10-phenanthrolinyl Ligands as Highly Active Catalysts for Ethylene Oligomerization", Organometallics 2006,25 2006,666-677.

Sun, Wen-Hua et al., "Synthesis, characterization and ethylene oligomerization studies of nickel complexes bearing 2-imino-1,10-phenanthrolines", Journal of Organometallic Chemistry 691 2006 , 4196-4203.

Scott, et al., "Metal versus Ligand Alkylation in the Reactivity of the (Bis-iminopyridinate)Fe Catalyst", Journal of American Chemical Society 127 2005 , 13109-13029.

Pelascini, et al., "Pyridine Bis(Imino) Iron and Cobalt Complexes for Ethylene Polymerization: Influence of the Aryl Imino Substituents", European Polymer Journal 41 2005 , 1288-1295.

Kooistra, et al., "Chemical Ligand Non-Innocence in Pyridine Diimine Rh Complexes", Inorganic Chimica Acta 357 2004 , 2945-2952.

Sugiyama, et al., "Preparation of an Active Neodymium Catalyst for REgioselective Butadiene cis-Polymerization Supported by a Dianionic Modification of the 2,6 Diiminopyridine Ligand", Organometallics 23 2004 , 5054-5061.

Chen, Y. et al., "Halogen-Substituted 2,6-Bis(imino)pyridyl Iron and Cobalt Complexes: Highly Active Catalysts for Polymerization and Oligomerization of Ethylene", Organometallics vol. 22(21) 2003 , 4312-4321.

Esteruelas, et al., "Preparation, Structure and Ethylene Polymerization Behavior of Bis(imino)oyridyl Chromium(III) Complexes", Organometallics ACS, Washington DC vol. 22 2003 , 395-406.

Reardon, et al., "Mono- and Zerovalent Manganese Alkyl Compexes Supported by the (alpha),(alpha-prime) Diiminato Pyradine Ligand: Alkyl Stabilization at the Expense of Catalytic Performance", Organometallics 21 2002 , 786-788.

Souane, R et al., "Pyridine Bis(imine) Cobalt or Iron Complexes for Ethylene and 1-Hexene (co)Polymerization", C.R.Chimie 5 2002 , 43-48.

Small, Brooke L. et al., "Highly Active Iron and Cobalt Catalysts for the Polymerization of Ethylene", J.Am. Chem. Soc. 1998 , 4049-4050.

Britovsek, G. et al., "Novel Olefin Polymerization Catalysts based on Iron and Cobalt", Chem. Commun. 1998, 849-850.

Ratzsch, M. et al., "Biomodal Polymer Materials Based on PP and PE", VDI-Verlag, Dusseldorf 1995, 3-25.

Hungenberg, K. D. et al., "Gas Phase Polymerization of [alpha]-Olefins with Ziegler-Natta and Metallocene Catalysts: a Comparison", Fink/Mulhaupt/Brintzinger (Eds.), Zielger Catalysts, Springer-Verlag Berlin Heidelberg BASF AG, Plastics Laboratory, D-67056 Ludwigshafen; 1995, 363-386.

Pang, S. et al., "Chapter 17—Size-Exclusion Chromatographic Assessment of Long-Chain Branch Frequency in Polyethylenes", American Chemical Society edited by Theodore Provder; ACS Symposium Series 521 (Chromatography of Polymers) 1993, 254-269.

Strauss, Steven H., "The Search for Larger and More Weakly Coordinating Anions", Chem. Rev. vol. 93(3) 1993, 927-942.

Bohm, Ludwig L. et al., "High-Density Polyethylene Pipe Resins", Advanced Materials 4 No. 3 1992, 234-238.

Falbe, et al., "Rompp Chemie Lexikon", Rompp Chemical Dictionary, 9th ed. Thieme vol. 6 1992, 5128-5129.

"Ullman's Encyclopedia of Industrial Chemistry", vol. A21, 4th Edition 1992, 502-504.

Randall, J., "A Review of High Resolution Liquid (13) Carbon Nuclear Magnetic Resonance Characterizations of Ethylene-Based Polymers", JMS-Rev. Macromol. Chem. Phys. C29 (2&3) 1989, 201-317.

Weisenfeldt, Helga, "ansa-Metallocene derivatives; XVII. Racemic and meso diastereomers of group IV metallocene derivatives with symmetrically substituted dimethylsilanediyl-bridged ligand frameworks. Crystal structure of R,S-Me2SI(3-1-Bu-5-MeC5H2)2ZrC12", Journal of Organometallic Chemistry, 369 Elsevier Sequoia S.A., Lausanne—Printed in the Netherlands 1989, 359-370.

Starzweski, K. O. et al., "Linear and Branched Polyethylenes by new Coordination Catalysts", Transition Metals and Organometallics as Catalysts for Olefin Polymerization Springer-Verlag Berlin Heidelberg 1988, 349-360.

Beach, D. et al., "Dual Functional Catalysis for Ethylene Polymerization to Branched Polyethylene. I Evaluation of Catalytic Systems", Journal of Polymer Science: Polymer Chemistry Edition vol. 22 1984, 3027-3042.

Hermann, C. et al., "Beeinflussung von titanhaltigen Polymerisations-katalysatoren durch zusatzliche Metalle", Die Angewandte Makromolekulare Chemie 94 1981, 91-104.

Holtrup, Wolfgang, "Zur Fraktionierung von Polymeren durch Direktextraktion", Makromol. Chem. 178 1977, 2335-2349.

Ogawa, S et al., "Preparation of a Conjugated Tautomer of 1, 14:7,88-Diethenotetrapyrido[2,1,6-de', 1',6'-gh:2",1"6"-k1:2"',1"',6"'-na][1,3,5,8,10,12]hexazacyclotetradecine and its Metal Derivatives", Journal of Chem. Soc. Perkin Trans. 1 1974, 976-978.

Benoit, H. Rempp et al., "A Universal Calibration for Gel Permeation Chromatography", Journal of Polymer Sci., Phys. Ed. 5 1967, 753-759.

Raff and Doak, "High Polymers", Interscience Publishers, John Wiley & Sons Vo. XX 1965, 442-443.

Fieser, Louis et al., "Textbook of Organic Chemistry, Third Revised Edition", Verlag Chemie-GmbH, Weinheim/Bergstr. 1957 1957, 10 pages.

Burkhardt, U. "Preparation of Polymers Having New Properties", Conference Baden-Baden Nov. 29-30, 1995/VDI-Gesellschaft Kunststofftechnik (Plastics Technology) Dusseldorf: VDI-VER1., 1995, ISBN 3-18-234191-X Aufbereiten von Polymeren mit neuartigen Eigenschaften Nov. 29, 1995, 3 pages.

Thabet, et al., "2-2'-[2,6-Pyridinediylbis(methylidynetirilio)]diphenol; A Highly Selective Reagent for the Detection of U(VI), Sb(III), and Bi(III)", Analytical Chemistry vol. 47, No. 11, Sep. 1975.

* cited by examiner

PROCESS FOR THE PREPARATION OF UNSYMMETRIC BIS(IMINO) COMPOUNDS

CROSS-REFERENCE TO RELATED APPLICATIONS

This application is a national phase filing under 35 U.S.C. §371 of International Application PCT/EP2007/000096, filed 8 Jan. 2007, claiming priority to German Patent Application 10 2006 001 959.8 filed 13 Jan. 2006 and provisional U.S. Appl. No. 60/811,013 filed 5 Jun. 2006; the disclosures of International Application PCT/EP2007/000096, German Pat. Appl. 10 2006 001 959.8, and U.S. Appl. No. 60/811,013, each as filed, are incorporated herein by reference.

The present invention relates to a process for the preparation of unsymmetric bis(imino) compounds.

The use of metallocene catalysts in the polymerization of unsaturated compounds shows a great influence on the preparation of polyolefins, since it opens up access to novel polyolefinic materials or to materials having improved properties. There is therefore great interest in the development of novel families of catalysts for the polymerization of unsaturated compounds in order to achieve an even better control over the properties of polyolefins or further novel products.

In particular, the use of transition metal catalysts with late transition metals is of interest because of their property of tolerating heteroatom functionalities. Transition metal catalysts of late transition metals which are suitable for the polymerization of unsaturated compounds are known from the prior art. 1,2-Diiminenickel and 2,6-bis(imino)pyridyliron complexes have proved to be particularly suitable here.

Unsymmetric 2,6-bis(imino)pyridyl compounds which carry two different imino groups are conventionally prepared via a first condensation of the corresponding diketo compounds with a primary amine. The intermediate product obtained is then reacted with a second primary amine which differs from the first. In the first step, in addition to the monoimine, the symmetric diimine product is also formed, so that the yield of the intermediate product is usually very low. The yield of monoimine intermediate product drops in particular if primary amines having electron-withdrawing groups or groups which cause little steric hindrance are used.

WO 98/27124 discloses the synthesis of unsymmetric 2,6-bis(imino)pyridyl compounds from the corresponding diketo compounds and anilines in toluene with the addition of catalytic amounts of toluenesulfonic acid, via monoimine intermediate products. Monoimine intermediate products having electron-withdrawing substituents are not disclosed. The preparation of unsymmetric 2,6-bis(imino)pyridyl compounds with anilines which carry an electron-withdrawing substituent in the ortho position gives only low yields of unsymmetric product in the second synthesis step.

The object of the present invention is to provide an improved process for the synthesis of unsymmetric bis(imino) compounds with which primary amines having electron-withdrawing substituents or substituents which cause little steric hindrance can also be converted into the corresponding monoimine compounds with better yields. These are particularly suitable starting materials for the synthesis of unsymmetric diimine compounds, and lead to higher yields of unsymmetric product. The unsymmetric diimine compounds having electron-withdrawing substituents show particularly high activities in the polymerization of alpha-olefins.

A process has accordingly been found for the preparation of monoimine compounds of the formula I

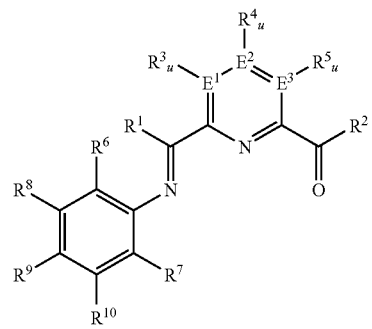

wherein the variables have the following meaning:

$R^1$-$R^2$ independently of one another denote hydrogen, $C_1$-$C_{22}$-alkyl, $C_2$-$C_{22}$-alkenyl, $C_6$-$C_{22}$-aryl, arylalkyl having 1 to 10 C atoms in the alkyl radical and 6-20 C atoms in the aryl radical, or five-, six- or seven-membered heterocyclyl, which comprises at least one atom from the group consisting of N, P, O or S, wherein the organic radicals $R^1$-$R^2$ can also be substituted by halogens, $NR^{11}_2$, $OR^{11}$ or $SiR^{12}_3$ and/or the two radicals $R^1$-$R^2$ can also be bonded with $R^3$-$R^5$ to form a five-, six- or seven-membered ring, $R^3$-$R^{10}$ independently of one another denote hydrogen, $C_1$-$C_{22}$-alkyl, $C_2$-$C_{22}$-alkenyl, $C_6$-$C_{22}$-aryl, arylalkyl having 1 to 10 C atoms in the alkyl radical and 6-20 C atoms in the aryl radical, $NR^{11}_2$, $OR^{11}$, halogen, CN, $SiR^{12}_3$ or five-, six- or seven-membered heterocyclyl, which comprises at least one atom from the group consisting of N, P, O or S, wherein the organic radicals $R^3$-$R^{10}$ can also be substituted by halogens, $NR^{11}_2$, $OR^{11}$ or $SiR^{12}_3$ and/or in each case two radicals $R^3$-$R^5$ can be bonded with one another or in each case two radicals $R^6$-$R^{10}$ can also be bonded with one another to form a five-, six- or seven-membered ring, and/or in each case two radicals $R^3$-$R^5$ are bonded with one another or in each case two radicals $R^6$-$R^{10}$ are bonded with one another to form a five-, six- or seven-membered heterocyclyl, which comprises at least one atom from the group consisting of N, P, O or S, $R^{11}$ independently of one another denote hydrogen, $C_1$-$C_{22}$-alkyl, $C_2$-$C_{22}$-alkenyl, $C_6$-$C_{22}$-aryl, arylalkyl having 1 to 10 C atoms in the alkyl radical and 6-20 C atoms in the aryl radical or $SiR^{12}_3$, wherein the organic radicals $R^{11}$ can also be substituted by halogens and in each case two radicals $R^{11}$ can also be bonded to form a five- or six-membered ring and $R^{12}$ independently of one another denote hydrogen, $C_1$-$C_{22}$-alkyl, $C_2$-$C_{22}$-alkenyl, $C_6$-$C_{22}$-aryl or arylalkyl having 1 to 10 C atoms in the alkyl radical and 6-20 C atoms in the aryl radical and in each case two radicals $R^{12}$ can also be bonded to form a five- or six-membered ring, $E^1$-$E^3$ independently of one another denote carbon, nitrogen or phosphorus, in particular carbon, and u independently of one another are 0 for $E^1$-$E^3$ as nitrogen or phosphorus and 1 for $E^1$-$E^3$ as carbon, wherein a dicarbonyl compound of the formula II

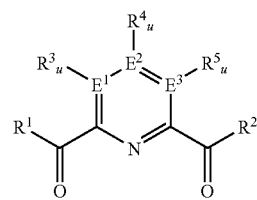

is reacted in an aliphatic, non-aromatic solvent with an aniline of the formula III

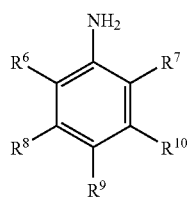

wherein the variables have the above meaning.

Specific monoimine compounds which give unsymmetric bis(imino) compounds by reaction with further aniline, iron complexes obtainable therefrom and the use thereof for the polymerization of olefins have furthermore been found.

In this context, the three atoms $E^1$ to $E^3$ can be identical or different. $E^1$ to $E^3$ are nitrogen, phosphorus or carbon, in particular nitrogen or carbon, and particularly preferably carbon.

The substituents $R^1$-$R^2$ of the monoimine compound of the formula I and of the dicarbonyl compound of the formula II can be varied within wide ranges. Possible C-organic substituents $R^1$-$R^2$ are, for example, the following: $C_1$-$C_{22}$-alkyl, wherein the alkyl can be linear or branched, such as e.g. methyl, ethyl, n-propyl, iso-propyl, n-butyl, iso-butyl, tert-butyl, n-pentyl, n-hexyl, n-heptyl, n-octyl, n-nonyl, n-decyl or n-dodecyl, 5- to 7-membered cycloalkyl, which in its turn can carry a $C_1$-$C_{10}$-alkyl group and/or $C_6$-$C_{10}$-aryl group as a substituent, such as e.g. cyclopropane, cyclobutane, cyclopentane, cyclohexane, cycloheptane, cyclooctane, cyclononane or cyclododecane, $C_2$-$C_{22}$-alkenyl, wherein the alkenyl can be linear, cyclic or branched and the double bond can be internal or terminal, such as e.g. vinyl, 1-allyl, 2-allyl, 3-allyl, butenyl, pentenyl, hexenyl, cyclopentenyl, cyclohexenyl, cyclooctenyl or cyclooctadienyl, $C_6$-$C_{22}$-aryl, wherein the aryl radical can be substituted by further alkyl groups, such as e.g. phenyl, naphthyl, biphenyl, anthranyl, o-, m-, p-methylphenyl, 2,3-, 2,4-, 2,5- or 2,6-dimethylphenyl or 2,3,4-, 2,3,5-, 2,3,6-, 2,4,5-, 2,4,6- or 3,4,5-trimethylphenyl, or arylalkyl, wherein the arylalkyl can be substituted by further alkyl groups, such as e.g. benzyl, o-, m-, p-methylbenzyl or 1- or 2-ethylphenyl, wherein two radicals $R^1$-$R^2$ can if appropriate also be bonded with $R^3$-$R^5$ to form a five-, six- or seven-membered ring, which can also be a heterocyclyl, which comprises at least one atom from the group consisting of N, P, O or S. The organic radicals $R^1$-$R^2$ can also be substituted by halogens, such as e.g. fluorine, chlorine or bromine, by amino $NR^{11}_2$, such as, for example, dimethylamino, N-pyrrolidinyl or picolinyl, by alkoxy or aryloxy $OR^{11}$, such as methoxy, ethoxy or isopropoxy, or Si-organic substituents $SiR^{12}_3$, such as e.g. trimethylsilyl, triethylsilyl, butyldimethylsilyl, tributylsilyl, tritert-butylsilyl, triallylsilyl, triphenylsilyl or dimethylphenylsilyl. Possible substituents $R^{11}$ are the same C-organic radicals as listed above in more detail for $R^1$-$R^2$, if appropriate it also being possible for two $R^{11}$ to be bonded to form a 5- or 6-membered ring and/or to be substituted by halogen. As Si-organic substituents $SiR^{12}_3$, the same C-organic radicals as listed above in more detail for $R^1$-$R^2$ are possible for $R^{12}$, if appropriate it also being possible for two $R^{12}$ to be bonded to form a 5- or 6-membered ring. Preferably, $R^1$ and $R^2$ are identical.

Preferred radicals $R^1$-$R^2$ are hydrogen, methyl, ethyl, n-propyl, iso-propyl, n-butyl, iso-butyl, tert-butyl, n-pentyl, n-hexyl, n-heptyl, n-octyl, benzyl or phenyl, and in particular methyl.

The substituents $R^3$-$R^{10}$ of the monoimine compound of the formula I, of the dicarbonyl compound of the formula II and of the aniline of the formula III can also be varied within wide ranges. Possible C-organic substituents $R^3$-$R^{10}$ are, for example, the following: $C_1$-$C_{22}$-alkyl, wherein the alkyl can be linear or branched, such as e.g. methyl, ethyl, n-propyl, iso-propyl, n-butyl, iso-butyl, tert-butyl, n-pentyl, n-hexyl, n-heptyl, n-octyl, n-nonyl, n-decyl or n-dodecyl, 5- to 7-membered cycloalkyl, which in its turn can carry a $C_1$-$C_{10}$-alkyl group and/or $C_6$-$C_{10}$-aryl group as a substituent, such as e.g. cyclopropane, cyclobutane, cyclopentane, cyclohexane, cycloheptane, cyclooctane, cyclononane or cyclododecane, $C_2$-$C_{22}$-alkenyl, wherein the alkenyl can be linear, cyclic or branched and the double bond can be internal or terminal, such as e.g. vinyl, 1-allyl, 2-allyl, 3-allyl, butenyl, pentenyl, hexenyl, cyclopentenyl, cyclohexenyl, cyclooctenyl or cyclooctadienyl, $C_6$-$C_{22}$-aryl, wherein the aryl radical can be substituted by further alkyl groups, such as e.g. phenyl, naphthyl, biphenyl, anthranyl, o-, m-, p-methylphenyl, 2,3-, 2,4-, 2,5- or 2,6-dimethylphenyl or 2,3,4-, 2,3,5-, 2,3,6-, 2,4,5-, 2,4,6- or 3,4,5-trimethylphenyl, or arylalkyl, wherein the arylalkyl can be substituted by further alkyl groups, such as e.g. benzyl, o-, m-, p-methylbenzyl or 1- or 2-ethylphenyl, wherein if appropriate also in each case two radicals $R^3$-$R^5$ can be bonded with one another or in each case two radicals $R^6$-$R^{10}$ can be bonded with one another to form a five-, six- or seven-membered ring and/or to form a five-, six- or seven-membered heterocyclyl, which comprises at least one atom from the group consisting of N, P, O or S, and/or wherein the organic radicals $R^3$-$R^{10}$ can also be substituted by halogens, such as e.g. fluorine, chlorine or bromine, amino $NR^{11}_2$, such as, for example, dimethylamino, N-pyrrolidinyl or picolinyl, alkoxy or aryloxy $OR^{11}$, such as methoxy, ethoxy or isopropoxy, or $SiR^{12}_3$. $R^3$-$R^{10}$ can furthermore be amino $NR^{11}_2$, such as, for example, dimethylamino, N-pyrrolidinyl or picolinyl, alkoxy or aryloxy $OR^{11}$, such as methoxy, ethoxy or isopropoxy, or halogens, such as e.g. fluorine, chlorine, bromine or iodine. Possible substituents $R^{11}$ are the same C-organic radicals as listed above in more detail for $R^1$-$R^2$, if appropriate it also being possible for two $R^{11}$ to be bonded to form a 5- or 6-membered ring and/or to be substituted by halogen. As Si-organic substituents $SiR^{12}_3$, the same C-organic radicals as listed above in more detail for $R^1$-$R^2$ are possible for $R^{12}$, if appropriate it also being possible for two $R^{12}$ to be bonded to a 5- or 6-membered ring, such as e.g. trimethylsilyl, triethylsilyl, butyldimethylsilyl, tributylsilyl, tritert-butylsilyl, triallylsilyl, triphenylsilyl or dimethylphenylsilyl.

Preferred radicals $R^3$-$R^5$ are hydrogen, methyl, trifluoromethyl, ethyl, n-propyl, iso-propyl, n-butyl, iso-butyl, tert-butyl, n-pentyl, n-hexyl, n-heptyl, n-octyl, benzyl, phenyl, fluorine, chlorine and bromine, and in particular hydrogen.

Preferred radicals $R^6$-$R^7$ are methyl, trifluoromethyl, ethyl, n-propyl, iso-propyl, n-butyl, iso-butyl, tert-butyl, n-pentyl, n-hexyl, n-heptyl, n-octyl, benzyl, phenyl, chlorine, bromine, iodine or methoxy. Particularly preferably, $R^6$ is chlorine, bromine or iodine and $R^7$ is a $C_1$-$C_{20}$-alkyl, wherein $R^7$ is preferably bonded with the aryl ring via a primary or secondary, preferably primary carbon atom.

Preferred radicals $R^8$ and $R^{10}$ are hydrogen, methyl, ethyl, n-propyl, fluorine, chlorine and bromine, and in particular hydrogen. Preferably, $R^8$ and $R^{10}$ are identical.

Preferred radicals $R^9$ are hydrogen, methyl, trifluoromethyl, ethyl, n-propyl, iso-propyl, n-butyl, iso-butyl, tert-butyl, n-pentyl, n-hexyl, n-heptyl, n-octyl, benzyl, phenyl, fluorine, chlorine and bromine, and in particular hydrogen, methyl, fluorine, chlorine or bromine, very particularly preferably chlorine. In the present application, a primary carbon atom is understood as meaning a carbon atom having the following substitution pattern —CH$_2$—R, wherein R denotes a linear, branched or cyclic alkyl, preferably C$_1$-C$_{19}$-alkyl, or hydrogen.

In the present application, a secondary carbon atom is understood as meaning a carbon atom having the following substitution pattern —CH—R$_2$, wherein R denotes a linear, branched or cyclic alkyl, preferably C$_1$-C$_{19}$-alkyl.

Preferred anilines of the formula III are 2-chloro-6-methylaniline, 2-bromo-6-methylaniline, 2,6-dichloroaniline, 2,4-dichloro-6-methylaniline or 2,6-dibromoaniline. Preferably, R$^6$ or R$^7$ is a halogen, in particular chlorine or bromine.

The molar ratio between the dicarbonyl compound and the aniline of the formula III employed is in general 1:5 to 1:0.8, preferably 1:2 to 1:0.9, and particularly preferably 1:1 to 1:1.2. The sequence of addition of the individual components is not critical here. Thus, for example, the dicarbonyl compound can be initially introduced into the reaction vessel and the aniline of the formula III can be added thereto.

A catalytic amount of an acid catalyst, such as, for example, C$_1$-C$_{10}$-carboxylic acids, such as formic acid or acetic acid, sulfonic acids, such as, for example, para-toluenesulfonic acid, and furthermore HCl, HBr, HI or H$_2$SO$_4$, is preferably added to the reaction. The molar ratio of dicarbonyl compound to acid catalyst is preferably in the range of from 1:0.00001 to 1:0.01, preferably from 1:0.0001 to 1:0.001. Reagents for absorption of the water formed during the reaction, such as, for example, a molecular sieve, phosphorus pentoxide or Si(OR)$_4$, wherein R is a C$_1$-C$_{10}$-alkyl, can furthermore be added.

The sequence of addition of the acid catalyst and/or of the reagent for absorption of water is not critical, and the addition is preferably made to the mixture of dicarbonyl compound and aniline.

Solvents which are conventionally used are aliphatic, non-aromatic hydrocarbons, such as, for example, pentane, such as n-pentane, hexane, such as n-hexane and iso-hexane, heptane, such as n-heptane, octane, such as n-octane, and mixtures thereof. Heptane is preferably used.

It has proved advantageous, in particular in the preparation of diimine compounds having halogen-containing substituents on the aniline, to carry out the synthesis under an inert gas atmosphere, such as nitrogen or argon.

The reaction is in general carried out at 18 to 150° C., preferably at 30 to 110° C., and particularly preferably at 50 to 90° C. The reaction time is conventionally between 30 minutes and 15 days, preferably between 5 hours and 5 days, particularly preferably between 8 hours and 3 days.

Working up is carried out in the conventional manner, e.g. by filtering off the product before or after removal of the solvent in vacuo. Purification of the product obtained can then be carried out by the conventional routes, such as, for example, by means of chromatography or recrystallization. An advantage of the reaction in aliphatic, non-aromatic solvents is the purity of the product obtained directly after filtration, which renders further working up unnecessary.

The process according to the invention is particularly suitable for anilines of the formula II having at least one halogen atom in the ortho position. Such anilines result in only low yields of monoimine compound in toluene or alcohol.

Monoimine compounds of the formula Ia have furthermore been found

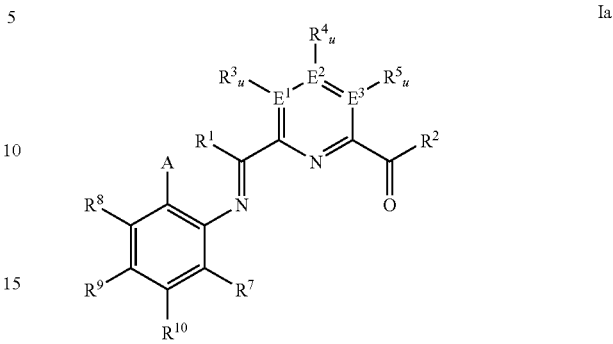

wherein the variables have the following meaning:
A is chlorine, bromine, iodine, CF$_3$ or OR$^{11}$,
R$^1$-R$^2$ independently of one another denote hydrogen, C$_1$-C$_{22}$-alkyl, C$_2$-C$_{22}$-alkenyl, C$_6$-C$_{22}$-aryl, arylalkyl having 1 to 10 C atoms in the alkyl radical and 6-20 C atoms in the aryl radical, or five-, six- or seven-membered heterocyclyl, which comprises at least one atom from the group consisting of N, P, O or S, wherein the organic radicals R$^1$-R$^2$ can also be substituted by halogens, NR$^{11}_2$, OR$^{11}$ or SiR$^{12}_3$ and/or the two radicals R$^1$-R$^2$ can also be bonded with R$^3$-R$^5$ to form a five-, six- or seven-membered ring,
R$^3$-R$^{10}$ independently of one another denote hydrogen, C$_1$-C$_{22}$-alkyl, C$_2$-C$_{22}$-alkenyl, C$_6$-C$_{22}$-aryl, arylalkyl having 1 to 10 C atoms in the alkyl radical and 6-20 C atoms in the aryl radical, NR$^{11}_2$, OR$^{11}$ halogen, SiR$^{12}_3$ or five-, six- or seven-membered heterocyclyl, which comprises at least one atom from the group consisting of N, P, O or S, wherein the organic radicals R$^3$-R$^{10}$ can be substituted by halogens, NR$^{11}_2$, OR$^{11}$ or SiR$^{12}_3$ and/or in each case two radicals R$^3$-R$^5$ can be bonded with one another or in each case two radicals R$^7$-R$^{10}$ can also be bonded with one another to form a five-, six- or seven-membered ring, and/or in each case two radicals R$^3$-R$^5$ are bonded with one another or in each case two radicals R$^7$-R$^{10}$ are bonded with one another to form a five-, six- or seven-membered heterocyclyl, which comprises at least one atom from the group consisting of N, P, O or S,
R$^{11}$ independently of one another denote hydrogen, C$_1$-C$_{22}$-alkyl, C$_2$-C$_{22}$-alkenyl, C$_6$-C$_{22}$-aryl, arylalkyl having 1 to 10 C atoms in the alkyl radical and 6-20 C atoms in the aryl radical or SiR$^{12}_3$, wherein the organic radicals R$^{11}$ can also be substituted by halogens and in each case two radicals R$^{11}$ can also be bonded to form a five- or six-membered ring,
R$^{12}$ independently of one another denote hydrogen, C$_1$-C$_{22}$-alkyl, C$_2$-C$_{22}$-alkenyl, C$_6$-C$_{22}$-aryl or arylalkyl having 1 to 10 C atoms in the alkyl radical and 6-20 C atoms in the aryl radical and in each case two radicals R$^{12}$ can also be bonded to form a five- or six-membered ring,
E$^1$-E$^3$ independently of one another denote carbon, nitrogen or phosphorus, in particular carbon, and
u independently of one another are 0 for E$^1$-E$^3$ as nitrogen or phosphorus and 1 for E$^1$-E$^3$ as carbon.

The definition of the variables R$^1$-R$^{12}$ and E$^1$-E$^3$ and preferred embodiments thereof is the same as described above for the monoimine compounds of the formula I.

A is preferably chlorine or bromine, in particular chlorine.
R$^7$ is preferably a C$_1$-C$_{20}$-alkyl. Particularly preferably, R$^7$ is bonded with the aryl ring via a primary or secondary, preferably primary carbon atom.

The monoimine compounds of the formula Ia obtained in this way can be reacted with further aniline of the formula III to give unsymmetric bis(imino) compounds of the formula IV.

Unsymmetric bis(imino) compounds of the formula IV have furthermore been found

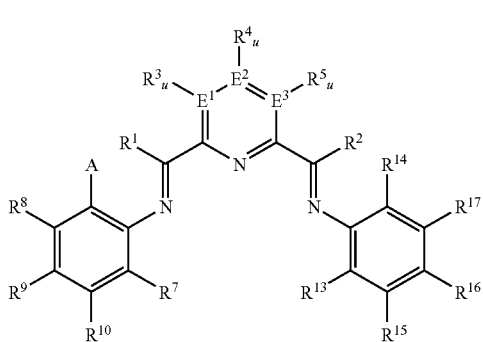

IV wherein the variables have the following meaning:

A is chlorine, bromine, iodine, $CF_3$ or $OR^{11}$, $R^1$-$R^2$ independently of one another denote hydrogen, $C_1$-$C_{22}$-alkyl, $C_2$-$C_{22}$-alkenyl, $C_6$-$C_{22}$-aryl, arylalkyl having 1 to 10 C atoms in the alkyl radical and 6-20 C atoms in the aryl radical, or five-, six- or seven-membered heterocyclyl, which comprises at least one atom from the group consisting of N, P, O or S, wherein the organic radicals $R^1$-$R^2$ can also be substituted by halogens, $NR^{11}_2$, $OR^{11}$ or $SiR^{12}_3$ and/or the two radicals $R^1$-$R^2$ can also be bonded with $R^3$-$R^5$ to form a five-, six- or seven-membered ring, $R^3$-$R^{10}$, $R^{13}$-$R^{17}$ independently of one another denote hydrogen, $C_1$-$C_{22}$-alkyl, $C_2$-$C_{22}$-alkenyl, $C_6$-$C_{22}$-aryl, arylalkyl having 1 to 10 C atoms in the alkyl radical and 6-20 C atoms in the aryl radical, $NR^{11}_2$, $OR^{11}$, halogen, $SiR^{12}_3$ or five-, six- or seven-membered heterocyclyl, which comprises at least one atom from the group consisting of N, P, O or S, wherein the organic radicals $R^3$-$R^{10}$ and $R^{13}$-$R^{17}$ can also be substituted by halogens, $NR^{11}_2$, $OR^{11}$ or $SiR^{12}_3$ and/or in each case two radicals $R^3$-$R^5$ can be bonded with one another and/or in each case two radicals $R^7$-$R^{10}$ can also be bonded with one another to form a five-, six- or seven-membered ring and/or in each case two radicals $R^{13}$-$R^{17}$ can also be bonded with one another to form a five-, six- or seven-membered ring, and/or in each case two radicals $R^3$-$R^5$ are bonded with one another and/or in each case two radicals $R^7$-$R^{10}$ are bonded with one another to form a five-, six- or seven-membered heterocyclyl and/or in each case two radicals $R^{13}$-$R^{17}$ are bonded with one another to form a five-, six- or seven-membered heterocyclyl, which comprises at least one atom from the group consisting of N, P, O or S, $R^{11}$ independently of one another denote hydrogen, $C_1$-$C_{22}$-alkyl, $C_2$-$C_{22}$-alkenyl, $C_6$-$C_{22}$-aryl, arylalkyl having 1 to 10 C atoms in the alkyl radical and 6-20 C atoms in the aryl radical or $SiR^{12}_3$, wherein the organic radicals $R^{11}$ can also be substituted by halogens and in each case two radicals $R^{11}$ can also be bonded to form a five- or six-membered ring, $R^{12}$ independently of one another denote hydrogen, $C_1$-$C_{22}$-alkyl, $C_2$-$C_{22}$-alkenyl, $C_6$-$C_{22}$-aryl or arylalkyl having 1 to 10 C atoms in the alkyl radical and 6-20 C atoms in the aryl radical and in each case two radicals $R^{12}$ can also be bonded to form a five- or six-membered ring, $E^1$-$E^3$ independently of one another denote carbon, nitrogen or phosphorus, in particular carbon, and u independently of one another are 0 for $E^1$-$E^3$ as nitrogen or phosphorus and 1 for $E^1$-$E^3$ as carbon.

The definition of the variables $R^1$-$R^{12}$ and $E^1$-$E^3$ and preferred embodiments thereof is the same as described above for the monoimine compounds of the formula I. The definition of the variables $R^{13}$-$R^{17}$ is the same as described above for the radicals $R^3$-$R^{10}$ of the monoimine compounds of the formula I.

According to the invention, unsymmetric bis(imino) compounds are understood as meaning those compounds which comprise at least two imino groups, the aryl radicals of which are not substituted in an identical manner. This relates to the substituents or the substitution pattern of the substituents, under the theoretical assumption that the aryl radicals can rotate freely.

$R^7$ is preferably a $C_1$-$C_{20}$-alkyl. Particularly preferably, $R^7$ is bonded with the aryl ring via a primary or secondary, preferably primary carbon atom.

Preferred radicals $R^{13}$-$R^{14}$ are hydrogen, methyl, trifluoromethyl, ethyl, n-propyl, iso-propyl, n-butyl, iso-butyl, tert-butyl, n-pentyl, n-hexyl, n-heptyl, n-octyl, benzyl, phenyl, fluorine, chlorine and bromine. Particularly preferably, the radicals $R^{13}$-$R^{14}$ are a $C_1$-$C_{20}$-alkyl, which is preferably bonded with the aryl ring via a primary or secondary, preferably primary carbon atom.

Preferred radicals $R^{15}$ and $R^{17}$ are hydrogen, methyl, ethyl, n-propyl, fluorine, chlorine and bromine, and in particular hydrogen. Preferably, $R^8$ and $R^{10}$ are identical.

Preferred radicals $R^{16}$ are hydrogen, methyl, trifluoromethyl, ethyl, n-propyl, iso-propyl, n-butyl, iso-butyl, tert-butyl, n-pentyl, n-hexyl, n-heptyl, n-octyl, benzyl, phenyl, fluorine, chlorine and bromine, and in particular hydrogen, methyl, fluorine, chlorine or bromine, very particularly preferably methyl.

A is preferably chlorine or bromine, in particular chlorine.

The preparation of the unsymmetric bis(imino) compounds of the formula IV from the monoimine compounds of the formula Ia and further aniline of the formula III can be carried out under the same conditions as have been described in more detail in the process according to the invention for the preparation of the monoimine compounds of the formula I.

The unsymmetric bis(imino) compounds of the formula IV can be converted into iron complexes of the formula V. These are suitable as catalysts for the polymerization of olefins.

Unsymmetric iron complexes of the formula V have therefore furthermore been found:

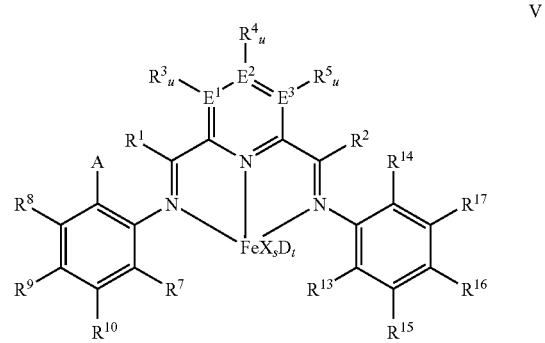

V wherein the variables have the following meaning:

A is chlorine, bromine, iodine, $CF_3$ or $OR^{11}$, $R^1$-$R^2$ independently of one another denote hydrogen, $C_1$-$C_{22}$-alkyl, $C_2$-$C_{22}$-alkenyl, $C_6$-$C_{22}$-aryl, arylalkyl having 1 to 10 C atoms in the alkyl radical and 6-20 C atoms in the aryl radical, or five-, six- or seven-membered heterocyclyl, which comprises at least one atom from the group consisting of N, P, O or S, wherein the organic radicals $R^1$-$R^2$ can also be substituted by halogens, $NR^{11}_2$, $OR^{11}$ or $SiR^{12}_3$ and/or the two radicals $R^1$-$R^2$ can also be bonded with $R^3$-$R^5$ to form a five-, six- or seven-membered ring, $R^3$-$R^{10}$, $R^{13}$-$R^{17}$ independently of one another denote hydrogen, $C_1$-$C_{22}$-alkyl, $C_2$-$C_{22}$-alkenyl, $C_6$-$C_{22}$-aryl, arylalkyl having 1 to 10 C atoms in the alkyl radical and 6-20 C atoms in the aryl radical, $NR^{11}_2$, $OR^{11}$, halogen, $SiR^{12}_3$ or five-, six- or seven-membered heterocyclyl, which comprises at least one atom from the group consisting of N, P, O or S, wherein the organic radicals $R^3$-$R^{10}$ and $R^{13}$-$R^{17}$ can also be substituted by halogens, $NR^{11}_2$, $OR^{11}$ or $SiR^{12}_3$ and/or in each case two radicals $R^3$-$R^5$ can be bonded with one another and/or in each case two radicals $R^7$-$R^{10}$ can also be bonded with one another to form a five-, six- or seven-membered ring and/or in each case two radicals $R^{13}$-$R^{17}$ can be bonded with one another to form a five-, six- or seven-membered ring, and/or in each case two radicals $R^3$-$R^5$ are bonded with one another and/or in each case two radicals $R^7$-$R^{10}$ are bonded with one another to form a five-, six- or seven-membered heterocyclyl and/or in each case two radicals $R^3$-$R^{17}$ are bonded with one another to form a five-, six- or seven-membered heterocyclyl, which comprises at least one atom from the group consisting of N, P, O or S, $R^{11}$ independently of one another denote hydrogen, $C_1$-$C_{22}$-alkyl, $C_2$-$C_{22}$-alkenyl, $C_6$-$C_{22}$-aryl, arylalkyl having 1 to 10 C atoms in the alkyl radical and 6-20 C atoms in the aryl radical or $SiR^{12}_3$, wherein the organic radicals $R^{11}$ can also be substituted by halogens and in each case two radicals $R^{11}$ can also be bonded to form a five- or six-membered ring, $R^{12}$ independently of one another denote hydrogen, $C_1$-$C_{22}$-alkyl, $C_2$-$C_{22}$-alkenyl, $C_6$-$C_{22}$-aryl or arylalkyl having 1 to 10 C atoms in the alkyl radical and 6-20 C atoms in the aryl radical and in each case two radicals $R^{12}$ can also be bonded to form a five- or six-membered ring, $E^1$-$E^3$ independently of one another denote carbon, nitrogen or phosphorus, in particular carbon, and u independently of one another are 0 for $E^1$-$E^3$ as nitrogen or phosphorus and 1 for $E^1$-$E^3$ as carbon, X independently of one another denote fluorine, chlorine, bromine, iodine, hydrogen, $C_1$-$C_{10}$-alkyl, $C_2$-$C_{10}$-alkenyl, $C_6$-$C_{20}$-aryl, arylalkyl having 1-10 C atoms in the alkyl radical and 6-20 C atoms in the aryl radical, $NR^{18}_2$, $OR^{18}$, $SR^{18}$, $SO_3R^{18}$, $OC(O)R^{18}$, CN, SCN, β-diketonate, CO, $BF_4^-$, $PF_6^-$ or bulky non-coordinating anions and the radicals X are if appropriate bonded with one another, $R^{18}$ independently of one another denote hydrogen, $C_1$-$C_{20}$-alkyl, $C_2$-$C_{20}$-alkenyl, $C_6$-$C_{20}$-aryl, arylalkyl having 1 to 10 C atoms in the alkyl radical and 6-20 C atoms in the aryl radical or $SiR^{19}_3$, wherein the organic radicals $R^{18}$ can also be substituted by halogens or nitrogen- and oxygen-containing groups and in each case two radicals $R^{18}$ can also be bonded to form a five- or six-membered ring, $R^{19}$ independently of one another denote hydrogen, $C_1$-$C_{20}$-alkyl, $C_2$-$C_{20}$-alkenyl, $C_6$-$C_{20}$-aryl or arylalkyl having 1 to 10 C atoms in the alkyl radical and 6-20 C atoms in the aryl radical, wherein the organic radicals $R^{19}$ can also be substituted by halogens or nitrogen- and oxygen-containing groups and in each case two radicals $R^{19}$ can also be bonded to form a five- or six-membered ring, s is 1, 2, 3 or 4, in particular 2 or 3, D is a neutral donor and t is 0 to 4, in particular 0, 1 or 2.

The definition of the variables $R^1$-$R^{12}$ and $E^1$-$E^3$ and preferred embodiments thereof is the same as described above for the monoimine compounds of the formula I. The definition of the variables $R^{13}$-$R^{17}$ is the same as described above for the radicals $R^3$-$R^{10}$ of the monoimine compounds of the formula I. The preferred embodiments of the variables $R^{13}$-$R^{17}$ is the same as described above for the radicals $R^{13}$-$R^{17}$ of the unsymmetric bis(imino) compounds of the formula IV.

A is preferably chlorine or bromine, in particular chlorine.

According to the invention, unsymmetric iron complexes are understood as meaning those compounds which comprise the unsymmetric bis(imino) compounds according to the invention having at least two imino groups, the aryl radicals of which are not substituted in an identical manner. This relates to the substituents or the substitution pattern of the substituents, under the theoretical assumption that the aryl radicals can rotate freely.

The ligands X result e.g. from the choice of the corresponding iron starting compounds which are used for the synthesis of the iron complexes, but can also additionally be varied subsequently. Possible ligands $X^C$ are, in particular, the halogens, such as fluorine, chlorine, bromine or iodine, and among these in particular chlorine and bromine. Alkyl radicals, such as methyl, ethyl, propyl, butyl, vinyl, allyl, phenyl or benzyl, are also ligands X which can be used. Further ligands X which may be mentioned only by way of example and in no way conclusively are trifluoroacetate, $BF_4^-$, $PF_6^-$ and weakly or non-coordinating anions (see e.g. S. Strauss in Chem. Rev. 1993, 93, 927-942), such as $B(C_6F_5)_4^-$. Amides, alcoholates, sulfonates, carboxylates and β-diketonates, in particular $R^{18}$—CO—C($R^{18}$)—CO—$R^{18}$, are also particularly suitable ligands X. Some of these substituted ligands X are particularly preferably used, since they are obtainable from cheap and easily accessible starting substances. A particularly preferred embodiment thus exists if X represents dimethylamide, methanolate, ethanolate, isopropanolate, phenolate, naphtholate, triflate, p-toluene sulfonate, acetate or acetyl acetonate.

By varying the radicals $R^{18}$ e.g. physical properties, such as solubility, can be finely adjusted. Possible C-organic substituents $R^{18}$ are, for example, the following: $C_1$-$C_{20}$-alkyl, wherein the alkyl can be linear or branched, such as e.g. methyl, ethyl, n-propyl, iso-propyl, n-butyl, iso-butyl, tert-butyl, n-pentyl, n-hexyl, n-heptyl, n-octyl, n-nonyl, n-decyl or n-dodecyl, 5- to 7-membered cycloalkyl, which in its turn can carry a $C_6$-$C_{10}$-aryl group as a substituent, such as e.g. cyclopropane, cyclobutane, cyclopentane, cyclohexane, cycloheptane, cyclooctane, cyclononane or cyclododecane, $C_2$-$C_{20}$-alkenyl, wherein the alkenyl can be linear, cyclic or branched and the double bond can be internal or terminal, such as e.g. vinyl, 1-allyl, 2-allyl, 3-allyl, butenyl, pentenyl, hexenyl, cyclopentenyl, cyclohexenyl, cyclooctenyl or cyclooctadienyl, $C_6$-$C_{20}$-aryl, wherein the aryl radical can be substituted by further alkyl groups and/or N- or O-containing radicals, such as e.g. phenyl, naphthyl, biphenyl, anthranyl, o-, m-, p-methylphenyl, 2,3-, 2,4-, 2,5- or 2,6-dimethylphenyl, 2,3,4-, 2,3,5-, 2,3,6-, 2,4,5-, 2,4,6- or 3,4,5-trimethylphenyl, 2-methoxyphenyl or 2-N,N-dimethylaminophenyl, or arylalkyl, wherein the arylalkyl can be substituted by further alkyl groups, such as e.g. benzyl, o-, m-, p-methylbenzyl or 1- or 2-ethylphenyl, wherein if appropriate also two $R^{18}$ can be bonded to form a 5- or 6-membered ring and the organic radicals $R^{18}$ can also be substituted by halogens, such as e.g. fluorine, chlorine or bromine. As Si-organic substituents $SiR^{19}_3$, the same radicals as listed above in more detail for $R^{18}$ are possible for $R^{19}$, if appropriate it also being possible for two $R^{19}$ to be bonded to form a 5- or 6-membered ring, such as e.g. trimethylsilyl, triethylsilyl, butyldimethylsilyl, tributylsilyl, triallylsilyl, triphenylsilyl or dimethylphenylsilyl. $C_1$-$C_{10}$-alkyl, such as methyl, ethyl, n-propyl, n-butyl, tert-butyl, n-pentyl, n-hexyl, n-heptyl and n-octyl, as well as vinyl, allyl, benzyl and phenyl are preferably used as radicals $R^{18}$.

The number s of ligands X depends on the oxidation level of the iron. The number s therefore cannot be stated in general terms. The oxidation level of the iron in catalytically active complexes is usually known to the person skilled in the art. However, complexes in which the oxidation level does not correspond to that of the active catalyst can also be employed. Such complexes can then be reduced or oxidized accordingly by suitable activators. Iron complexes in the oxidation level +3 or +2 are preferably used.

D is a neutral donor, in particular a neutral Lewis base or Lewis acid, such as, for example, amines, alcohols, ethers, ketones, aldehydes, esters, sulfides or phosphines, which can be bonded with the iron center or can still be contained in the complex as residual solvent from the preparation of the iron complexes.

The number t of the ligands D can be a number between 0 and 4 and often depends on the solvent in which the iron complex is prepared and on how long the resulting complexes are dried, and therefore also may denote a number which is not an integer, such as 0.5 or 1.5. In particular, t is 0, 1 to 2.

Particularly preferred unsymmetric bisimine compounds of the formula IV are 2-[1-(2,6-dimethylphenylimino)-ethyl]-6-[1-(2-chloro-4,6-dimethylphenylimino)ethyl]pyridine, 2-[1-(2,4,6-trimethylphenylimino)ethyl]-6-[1-(2-chloro-4,6-dimethylphenylimino)ethyl]pyridine, 2-[1-(2,6-dimethyl-phenylimino)ethyl]-6-[1-(2,4-dichloro-6-methylphenylimino)ethyl]pyridine, 2-[1-(2,4,6-trimethylphenylimino)ethyl]-6-[1-(2,4-dichloro-6-methylphenylimino)ethyl]pyridine, 2-[1-(2,6-dimethylphenylimino)ethyl]-6-[1-(2-chloro-6-methylphenylimino)ethyl]pyridine, 2-[1-(2,4,6-trimethylphenylimino)ethyl]-6-[1-(2-chloro-6-methylphenylimino)ethyl]pyridine, 2-[1-(2,6-diisopropylphenylimino)ethyl]-6-[1-(2-chloro-6-methyl-phenylimino)ethyl]pyridine, 2-[1-(2,6-dimethylphenylimino)ethyl]-6-[1-(2-bromo-4,6-dimethyl-phenylimino)ethyl]pyridine, 2-[1-(2,4,6-trimethylphenylimino)ethyl]-6-[1-(2-bromo-4,6-dimethyl-phenylimino)ethyl]pyridine, 2-[1-(2,6-dimethylphenylimino)ethyl]-6-[1-(2-bromo-6-methyl-phenylimino)ethyl]pyridine, 2-[1-(2,4,6-trimethylphenylimino)ethyl]-6-[1-(2-bromo-6-methylphenylimino)ethyl]pyridine and 2-[1-(2,6-diisopropylphenylimino)ethyl]-6-[1-(2-bromo-6-methylphenylimino)ethyl]pyridine.

The preparation of the iron complexes is described, for example, in J. Am. Chem. Soc. 120, p. 4049 et seq. (1998), J. Chem. Soc., Chem. Commun. 1998, 849 and WO 98/27124. Preferred iron complexes of the formula V are 2-[1-(2,6-dimethylphenylimino)ethyl]-6-[1-(2-chloro-4,6-dimethylphenylimino)ethyl]pyridineiron dichloride, 2-[1-(2,4,6-trimethylphenylimino)ethyl]-6-[1-(2-chloro-4,6-dimethylphenylimino)ethyl]pyridineiron dichloride, 2-[1-(2,6-dimethylphenylimino)ethyl]-6-[1-(2,4-dichloro-6-methylphenylimino)ethyl]pyridineiron dichloride, 2-[1-(2,4,6-trimethylphenylimino)ethyl]-6-[1-(2,4-dichloro-6-methylphenylimino)ethyl]pyridineiron dichloride, 2-[1-(2,6-dimethylphenylimino)ethyl]-6-[1-(2-chloro-6-methylphenylimino)ethyl]pyridineiron dichloride, 2-[1-(2,4,6-trimethylphenylimino)ethyl]-6-[1-(2-chloro-6-methylphenylimino)ethyl]pyridineiron dichloride, 2-[1-(2,6-diisopropylphenylimino)ethyl]-6-[1-(2-chloro-6-methylphenylimino)ethyl]pyridineiron dichloride, 2-[1-(2,6-dimethylphenylimino)ethyl]-6-[1-(2-bromo-4,6-dimethylphenylimino)ethyl]pyridineiron dichloride, 2-[1-(2,4,6-trimethylphenylimino)ethyl]-6-[1-(2-bromo-4,6-dimethylphenylimino)ethyl]pyridineiron dichloride, 2-[1-(2,6-dimethylphenylimino)ethyl]-6-[1-(2-bromo-6-methylphenylimino)ethyl]pyridineiron dichloride, 2-[1-(2,4,6-trimethylphenylimino)ethyl]-6-[1-(2-bromo-6-methylphenylimino)ethyl]pyridineiron dichloride and 2-[1-(2,6-diisopropylphenylimino)ethyl]-6-[1-(2-bromo-6-methylphenylimino)ethyl]pyridineiron dichloride or the particular dibromides or tribromides.

With the processes according to the invention, in particular, anilines having electron-withdrawing substituents can also be converted into the corresponding monoimine compounds in good yields. Furthermore, the working up of the monoimine compounds obtained is considerably simpler, and filtering off of the precipitate formed, which usually comprises exclusively the monoimine compound, is often sufficient.

The monoimine compounds Ia are thermodynamically very stable and can be reacted with further aniline to give the unsymmetric bisimine compounds IV. If monoimine compounds which are not substituted by electron-withdrawing radicals in the ortho position are used as starting substances, a further reaction with further aniline usually leads to mixtures of various symmetric and unsymmetric bisimine compounds.

The unsymmetric iron complexes V show very high polymerization activities. They furthermore show narrow molar mass distributions and molecular weights in a range which is favorable for many uses.

The iron complexes V according to the invention can be used by themselves or with further components as a catalyst system for the olefin polymerization. Catalyst systems for olefin polymerization comprising at least one iron complex of the formula V, optionally an organic or inorganic support, optionally one or more activators, optionally one or more metal compounds of group 1, 2 or 13 of the periodic table and optionally further catalysts suitable for olefin polymerization have therefore furthermore been found.

The iron complex V in itself in some cases has only a low polymerization activity, and can then be brought into contact with one or more activators in order to be able to display a good polymerization activity. The catalyst system therefore furthermore optionally comprises one or more activating compounds, preferably one or two activating compounds.

The activator or the activators can in each case be employed in any desired amounts, based on the iron complex V, and they are preferably employed in an excess or in stoichiometric amounts. The amount of activating compound(s) to be used depends on the nature of the activator. The molar ratio of iron complex V to activating compound is conventionally in the range of from 1:0.1 to 1:10,000, preferably from 1:1 to 1:2000.

Suitable activators are e.g. compounds of the type of an aluminoxane, a strong neutral Lewis acid, an ionic compound having a Lewis acid cation or an ionic compound having a Brönsted acid as a cation.

The compounds described in WO 00/31090, for example, can be employed as aluminoxanes. Open-chain or cyclic aluminoxane compounds of the general formulae (X) or (XI) are particularly suitable

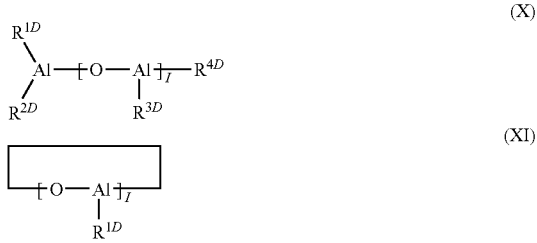

wherein $R^{1D}$-$R^{4D}$ independently of one another denote a $C_1$-$C_6$-alkyl group, preferably a methyl, ethyl, butyl or isobutyl group, and I represents an integer from 1 to 40, preferably 4 to 25.

Methylaluminoxane is a particularly suitable aluminoxane compound.

The preparation of these oligomeric aluminoxane compounds is conventionally carried out by controlled reaction of a solution of trialkylaluminum, in particular trimethylaluminum, with water. As a rule, the oligomeric aluminoxane compounds obtained in this reaction are in the form of mixtures of both linear and cyclic chain molecules of different length, so that I is to be regarded as a mean value. The aluminoxane compounds can also be in the form of a mixture with other metal-alkyls, conventionally with aluminum-alkyls. Aluminoxane formulations which are suitable as activators are commercially obtainable.

Instead of the aluminoxane compounds of the general formulae (X) or (XI), modified aluminoxanes in which the hydrocarbon radicals are in some cases replaced by hydrogen atoms or alkoxy, aryloxy, siloxy or amide radicals can furthermore also be employed as the activator.

It has proved advantageous to use the iron complex V and the aluminoxane compounds in amounts such that the atomic ratio between aluminum from the aluminoxane compounds, including aluminum-alkyl still contained therein, and the iron from the iron complex V is conventionally in the range of from 1:1 to 2000:1, preferably from 10:1 to 500:1, and in particular in the range of from 20:1 to 400:1.

A further type of suitable activators are the so-called hydroxyaluminoxanes. These can be prepared, for example, by addition of from 0.5 to 1.2 equivalents of water, preferably 0.8 to 1.2 equivalents of water per equivalent of aluminum to an alkylaluminum compound, in particular triisobutylaluminum, at low temperatures, conventionally below 0° C. Such compounds and their use in olefin polymerization are described, for example, in WO 00/24787. The atomic ratio between aluminum from the hydroxyaluminoxane compound and the iron from the iron complex V is conventionally in the range of from 1:1 to 100:1, preferably from 10:1 to 50:1, and in particular in the range of from 20:1 to 40:1.

Preferred strong, neutral Lewis acids are compounds of the general formula (XII)

$$M^{2D}X^{1D}X^{2D}X^{3D} \quad (XII)$$

in which
$M^{2D}$ denotes an element of group 13 of the periodic table of the elements, in particular B, Al or Ga, preferably B,
$X^{1D}$, $X^{2D}$ and $X^{3D}$ represent hydrogen, $C_1$-$C_{10}$-alkyl, $C_6$-$C_{15}$-aryl, alkylaryl, arylalkyl, haloalkyl or haloaryl having in each case 1 to 10 C atoms in the alkyl radical and 6 to 20 C atoms in the aryl radical, or fluorine, chlorine, bromine or iodine, in particular haloaryls, preferably pentafluorophenyl.

Further examples of strong, neutral Lewis acids are mentioned in WO 00/31090.

Boranes and boroxines, such as e.g. trialkylborane, triarylborane or trimethylboroxine, are suitable in particular as activators. Boranes which carry at least two perfluorinated aryl radicals are particularly preferably employed. Compounds of the general formula (XII) in which $X^{1D}$, $X^{2D}$ and $X^{3D}$ are identical, for example triphenylborane, tris(4-fluorophenyl)borane, tris(3,5-difluorophenyl)borane, tris(4-fluoromethyl-phenyl)borane, tris(pentafluorophenyl)borane, tris(tolyl)borane, tris(3,5-dimethylphenyl)borane, tris(3,5-difluorophenyl)borane or tris(3,4,5-trifluorophenyl)borane, are particularly preferred. Tris(pentafluorophenyl)borane is preferably used.

Suitable activators are preferably prepared from the reaction of aluminum or boron compounds of the formula (XII) with water, alcohols, phenol derivatives, thiophenol derivatives or aniline derivatives, the halogenated, and especially the perfluorinated alcohols and phenols being of importance in particular. Examples of particularly suitable compounds are pentafluorophenol, 1,1-bis-(pentafluorophenyl)methanol or 4-hydroxy-2,2',3,3',4',5,5',6,6'-nonafluorobiphenyl. Examples of the combination of compounds of the formula (XII) with Broenstedt acids are, in particular, trimethylaluminum/pentafluorophenol, trimethylaluminum/1-bis(pentafluorophenyl)methanol, trimethylaluminum/4-hydroxy-2, 2', 3,3', 4', 5,5',6,6'-nonafluorobiphenyl, triethylaluminum/pentafluorophenol or triisobutylaluminum/pentafluorophenol or triethylaluminium/4,4'-dihydroxy-2,2', 3,3',5,5',6,6'-octafluorobiphenyl hydrate.

In further suitable aluminum and boron compounds of the formula (XII), $R^{1D}$ is an OH group, such as, for example, in boron acids and boric acids, boric acids having perfluorinated aryl radicals, such as, for example, $(C_6F_5)_2BOH$, being mentioned in particular.

Strong neutral Lewis acids which are suitable as activators are also the reaction products from the reaction of a boron acid with two equivalents of an aluminum-trialkyl or the reaction products from the reaction of an aluminum-trialkyl with two equivalents of an acid fluorinated, in particular perfluorinated carbon compound, such as pentafluorophenol or bis-(pentafluorophenyl)boric acid.

Suitable ionic compounds having Lewis acid cations are salt-like compounds of the cation of the general formula (XIII)

$$[((M^{3D})^{a+})Q_1Q_2\ldots Q_z]^{d+} \quad (XIII)$$

in which
$M^{3D}$ denotes an element of group 1 to 16 of the periodic table of the elements,
$Q_1$ to $Q_z$ represent singly negatively charged radicals, such as $C_1$-$C_{28}$-alkyl, $C_6$-$C_{15}$-aryl, alkylaryl, arylalkyl, haloalkyl or haloaryl having in each case 6 to 20 C atoms in the aryl and 1 to 28 C atoms in the alkyl radical, $C_3$-$C_{10}$-cycloalkyl, which can if appropriate be substituted by $C_1$-$C_{10}$-alkyl groups, halogen, $C_1$-$C_{28}$-alkoxy, $C_6$-$C_{15}$-aryloxy or silyl or mercaptyl groups,
a represents integers from 1 to 6 and
z represents integers from 0 to 5 and
d corresponds to the difference a-z, but wherein d is greater than or equal to 1.

Carbonium cations, oxonium cations and sulfonium cations as well as cationic transition metal complexes are particularly suitable. The triphenylmethyl cation, the silver cation and the 1,1'-dimethylferrocenyl cation are to be mentioned in particular. They preferably have non-coordinating counterions, in particular boron compounds such as are also mentioned in WO 91/09882, preferably tetrakis(pentafluoro-phenyl)borate.

Salts with non-coordinating anions can also be prepared by bringing together a boron or aluminum compound, e.g. an aluminum-alkyl, with a second compound which can link two or more boron or aluminum atoms by reaction, e.g. water, and a third compound which forms an ionizing ionic compound with the boron compound or aluminum compound, e.g. triphenylchloromethane, or optionally a base, preferably an organic nitrogen-containing base, such as, for example, an amine, an aniline derivative or a nitrogen heterocyclyl. A fourth compound, which likewise reacts with the boron compound or aluminum compound, e.g. pentafluorophenol, can additionally be added.

Ionic compounds having Brönsted acids as cations preferably likewise have non-coordinating counterions. Protonated amine or aniline derivatives are preferred in particular as the Brönsted acid. Preferred cations are N,N-dimethylanilinium, N,N-dimethylcyclo-hexylammonium and N,N-dimethylbenzylammonium as well as derivatives of the two mentioned last.

Compounds having anionic boron heterocyclyls, such as are described in WO 9736937, are also suitable as activators, in particular dimethylanilinium boratabenzenes or trityl boratabenzenes Preferred ionic activators comprise borates which carry at least two perfluorinated aryl radicals. Particularly preferred compounds are N,N-dimethylanilinium tetrakis-(pentafluorophenyl)borate, and especially N,N-dimethyl-cyclohexylammonium tetrakis(pentafluorophenyl)borate, N,N-dimethylbenzylammonium tetrakis(pentafluorophenyl)-borate or trityl tetrakispentafluorophenylborate.

It is also possible for two or more borate anions to be bonded with one another, as in the dianion $[(C_6F_5)_2B—C_6F_4—B(C_6F_5)_2]^{2-}$, or the borate anion can be bonded via a bridge with a suitable functional group on the support surface.

Further suitable activators are listed in WO 00/31090.

The amount of strong, neutral Lewis acids, ionic compounds having Lewis acid cations or ionic compounds having Brönsted acids as cations is preferably 0.1 to 20 equivalents, preferably 1 to 10 equivalents, and particularly preferably 1 to 2 equivalents, based on the iron complex V.

Suitable activators are also boron-aluminum compounds, such as di[bis(pentafluorophenylboroxy)]methylalane. Corresponding boron-aluminum compounds are disclosed, for example, in WO 99/06414.

Mixtures of all the abovementioned activating compounds can also be employed. Preferred mixtures comprise aluminoxanes, in particular methylaluminoxane, and an ionic compound, in particular one which comprises the tetrakis(pentafluorophenyl)borate anion, and/or a strong neutral Lewis acid, in particular tris(pentafluorophenyl)borane or a boroxine.

Preferably, the iron complex V and also the activator(s) are employed in a solvent, aromatic hydrocarbons having 6 to 20 C atoms, in particular xylenes, toluene, pentane, hexane, heptane or mixtures of these, being preferred.

There is furthermore the possibility of employing an activator which can simultaneously be used as the support. Such systems are obtained, for example, from an inorganic oxide treated with zirconium alkoxide, and subsequent chlorination, e.g. with carbon tetrachloride. The preparation of such systems is described, for example, in WO 01/41920.

In particular, the combinations of the preferred embodiments of the activators with the preferred embodiments of the iron complexes V are preferred.

An aluminoxane is preferably employed as the activator for the iron complexes V. The combination of salt-like compounds of the cation of the general formula (XIII), in particular N,N-dimethylanilinium tetrakis-(pentafluorophenyl)borate, N,N-dimethylcyclohexyl-ammonium tetrakis (pentafluorophenyl)borate, N,N-dimethylbenzylammonium tetrakis(pentafluorophenyl)-borate or trityl tetrakispentafluorophenylborate, as the activator for the iron complex V, in particular in combination with an aluminoxane is furthermore preferred.

So that the iron complex V can be employed in the polymerization process in the gas phase or in suspension, it is often of advantage for the complexes to be employed in the form of a solid, i.e. for them to be applied to a solid support. The supported complexes furthermore have a high productivity. The iron complexes V can therefore optionally also be immobilized on an organic or inorganic support and used in the polymerization in the supported form. As a result, for example, reactor deposits can be avoided and the polymer morphology can be controlled. Support materials which are preferably used are silica gel, magnesium chloride, aluminum oxide, mesoporous materials, aluminosilicates, hydrotalcites and organic polymers, such as polyethylene, polypropylene, polystyrene, polytetrafluoroethylene or polymers functionalized with polar groups, such as, for example, copolymers of ethene and acrylate, acrolein or vinyl acetate.

A catalyst system comprising at least one iron complex V, at least one activator and at least one support component is particularly preferred.

Preferably, for the preparation of the catalyst systems according to the invention, the iron complex V and/or the activator are fixed on the support by physisorption or also by a chemical reaction, which means covalent bonding of the components with reactive groups of the support surface.

In principle, any desired sequence is possible for bringing together the support component, the iron complex V and the activator. After the individual process steps, the various intermediate stages can be washed with suitable inert solvents, such as e.g. aliphatic or aromatic hydrocarbons.

The iron complex V and the activator can be fixed independently of one another, e.g. successively or simultaneously. Thus, the support component can be brought into contact first with the activator or activators or also first with the iron complex V. Preactivation of the iron complex V with one or more activators before thorough mixing with the support is also possible. In one possible embodiment, the iron complex V can also be prepared in the presence of the support material. A further type of immobilization is also prepolymerization of the catalyst system with or without prior application to a support.

The immobilization is as a rule carried out in an inert solvent, which can be filtered off or evaporated after the immobilization. After the individual process steps, the solid catalyst system can be washed with suitable inert solvents, such as e.g. aliphatic or aromatic hydrocarbons, and dried. However, it is also possible to use the still moist, supported catalyst system.

In a preferred form of the preparation of the supported catalyst system, at least one iron complex V is brought into contact with at least one activator and the mixture is then mixed with the dehydrated or inertized support material. Preferably, the resulting supported catalyst system is dried, in order to ensure that all or most of the solvent is removed from the pores of the support material. The supported catalyst is preferably obtained as a free-flowing powder. Examples of the industrial realization of the above process are described in WO 96/00243, WO 98/40419 or WO 00/05277. A further preferred embodiment is first to produce the activator on the support component or to apply it to this and subsequently to bring this supported compound into contact with the iron complex V.

Finely divided supports, which can be any desired organic or inorganic solid, are preferably employed as the support component. In particular, the support component can be a porous support, such as talc, a laminar silicate, such as montmorillonite or mica, an inorganic oxide or a finely divided polymer powder (e.g. polyolefin or polymer functionalized with polar groups).

The support materials used preferably have a specific surface area in the range of from 10 to 1000 m$^2$/g, a pore volume in the range of from 0.1 to 5 ml/g and an average particle size of from 1 to 500 µm. Supports having a specific surface area in the range of from 50 to 700 m$^2$/g, a pore volume in the range between 0.4 and 3.5 ml/g and an average particle size in the range of from 5 to 350 µm are preferred. Supports having a specific surface area in the range of from 200 to 550 m$^2$/g, a pore volume in the range between 0.5 to 3.0 ml/g and an average particle size of from 10 to 150 µm are particularly preferred.

The iron complex V is preferably applied in an amount such that the concentration of iron from the iron complex V in the finished catalyst system is 1 to 200 µmol, preferably 5 to 100 µmol, and particularly preferably 10 to 70 µmol per g of finished catalyst system.

The inorganic support can be subjected to a heat treatment, e.g. to remove adsorbed water. Such a drying treatment is as a rule carried out at temperatures in the range of from 50 to 1000° C., preferably from 100 to 600° C., drying at 100 to 200° C. preferably being carried out in vacuo and/or under an inert gas blanket (e.g. nitrogen), or the inorganic support can be calcined at temperatures of from 200 to 1000° C. in order to establish, if appropriate, the desired structure of the solid and/or the desired OH concentration on the surface. The support can also be treated chemically, it being possible to employ conventional drying agents, such as metal-alkyls, preferably aluminum-alkyls, chlorosilanes or SiCl$_4$, but also methylalumoxane. Corresponding treatment methods are described, for example, in WO 00/31090.

The inorganic support material can also be modified chemically. For example, treatment of silica gel with NH$_4$SiF$_6$ or other fluorinating agents leads to fluorination of the silica gel surface, or treatment of silica gels with silanes which comprise nitrogen-, fluorine- or sulfur-containing groups leads to correspondingly modified silica gel surfaces.

Organic support materials, such as finely divided polyolefin powders (e.g. polyethylene, polypropylene or polystyrene) can also be used and should preferably likewise be freed from adhering moisture, solvent residues or other impurities by appropriate purification and drying operations before use. It is also possible to employ functionalized polymer supports, e.g. based on polystyrene, polyethylene, polypropylene or polybutylene, via the functional groups of which, for example ammonium or hydroxyl groups, at least one of the catalyst components can be fixed. Polymer blends can also be used.

Suitable inorganic oxides as the support component are to be found in groups 2, 3, 4, 5, 13, 14, 15 and 16 of the periodic table of the elements. Examples of oxides which are preferred as the support include silicon dioxide, aluminum oxide and mixed oxides of the elements calcium, aluminum, silicon, magnesium or titanium, as well as corresponding oxide mixtures. Other inorganic oxides, which can be employed by themselves or in combination with the preferred oxidic supports mentioned last, are e.g. MgO, CaO, AlPO$_4$, ZrO$_2$, TiO$_2$, B$_2$O$_3$ or mixtures thereof.

Further preferred inorganic support materials are inorganic halide, such as MgCl$_2$, or carbonates, such as e.g. Na$_2$CO$_3$, K$_2$CO$_3$, CaCO$_3$ or MgCO$_3$, sulfates, such as Na$_2$SO$_4$, Al$_2$(SO$_4$)$_3$ or BaSO$_4$, and nitrates, such as e.g. KNO$_3$, Mg(NO$_3$)$_2$ or Al(NO$_3$)$_3$.

Silica gels are preferably used as solid support materials for catalysts for the olefin polymerization, since particles which are suitable in size and structure as a support for the olefin polymerization can be prepared from this material. In this context, spray-dried silica gels, which are spherical agglomerate of smaller granular particles, the so-called primary particles, have proved to be particularly appropriate. The silica gels can be dried and/or calcined here before their use.

Hydrotalcites and calcined hydrotalcites are likewise preferred supports. In mineralogy, a natural mineral having the ideal formula $$Mg_6Al_2(OH)_{16}CO_3 \cdot 4H_2O$$

the structure of which is derived from that of brucite Mg(OH)$_2$, is called hydrotalcite. Brucite crystallizes in a layered structure with the metal ions in octahedral voids between two layers of densely packed hydroxyl ions, only every second layer of the octahedral voids being occupied. In hydrotalcite, some magnesium ions are replaced by aluminum ions, as a result of which the layer package acquires a positive charge. This is compensated by the anions in the intermediate layers together with water of crystallization.

Corresponding layered structures are found not only in magnesium-aluminum hydroxides, but generally in mixed metal hydroxides built up in the form of layers, of the general formula $$M(II)_{2x}^{2+}M(III)_2^{3+}(OH)_{4x+4} \cdot A_{2/n}^{n-} \cdot zH_2O$$

in which M(II) is a divalent metal, such as Mg, Zn, Cu, Ni, Co, Mn, Ca and/or Fe, and M(III) is a trivalent metal, such as Al, Fe, Co, Mn, La, Ce and/or Cr, x represents numbers from 0.5 to 10 in steps of 0.5, A represents an interstitial anion and n represents the charge of the interstitial anion, which can be from 1 to 8, conventionally from 1 to 4, and z is an integer from 1 to 6, in particular from 2 to 4. Possible interstitial anions are organic anions, such as alcoholate anions, alkyl ether sulfates, aryl ether sulfates or glycol ether sulfates, inorganic anions, such as, in particular, carbonate, bicarbonate, nitrate, chloride, sulfate or B(OH)$_4^-$, or polyoxometal anions, such as Mo$_7$O$_{24}^{6-}$ or V$_{10}$O$_{28}^{6-}$. However, there can also be a mixture of several such anions.

All mixed metal hydroxides built up in such a manner in the form of layers should accordingly be understood as hydrotalcites in the context of the present invention.

The so-called calcined hydrotalcites can be prepared from hydrotalcites by calcining, i.e. heating, as a result of which, inter alia, the desired content of hydroxyl groups can be established. The structure of the crystal construction furthermore also changes. The preparation of the calcined hydrotalcites employed according to the invention is conventionally carried out at temperatures above 180° C. Calcining for a period of time of from 3 to 24 hours at temperatures of from 250° C. to 1000° C. and in particular from 400° C. to 700° C. is preferred. It is possible to simultaneously pass over air or an inert gas or to apply a vacuum.

On heating, the natural or synthetic hydrotalcites initially release water, i.e. drying takes place. On further heating, the actual calcining, the metal hydroxides are converted into the metal oxides by hydroxyl groups and interstitial anions being split off, it also being possible for the calcined hydrotalcites still to comprise OH groups or interstitial anions, such as carbonate. The loss on ignition is a measure of this. This is the weight loss which a sample suffers when heated in two steps, first for 30 min at 200° C. in a drying cabinet and then for 1 hour at 950° C. in a muffle oven.

The calcined hydrotalcites employed as a component are thus mixed oxides of the di- and trivalent metals M(II) and M(III), wherein the molar ratio of M(II) to M(III) is as a rule in the range of from 0.5 to 10, preferably from 0.75 to 8, and in particular from 1 to 4. Conventional amounts of impurities, for example of Si, Fe, Na, Ca or Ti, and also chlorides and sulfates, can furthermore also be present.

Preferred calcined hydrotalcites are mixed oxides in which M(II) is magnesium and M(III) is aluminum. Corresponding aluminum-magnesium mixed oxides are obtainable from Condea Chemie GmbH (now Sasol Chemie), Hamburg under the trade name Puralox Mg.

Calcined hydrotalcites in which the structural conversion is virtually or completely concluded are furthermore preferred. A calcining, i.e. a conversion of the structure, can be detected, for example, from X-ray diffractograms.

The hydrotalcites, calcined hydrotalcites or silica gels employed are as a rule employed as finely divided powders having an average particle diameter D50 of from 5 to 200 µm, preferably from 10 to 150 µm, particularly preferably from 15 to 100 µm, and in particular from 20 to 70 µm, and conventionally have pore volumes of from 0.1 to 10 cm$^3$/g, preferably from 0.2 to 5 cm$^3$/g, and specific surface areas of from 30 to 1000 m$^2$/g, preferably from 50 to 800 m$^2$/g, and in particular from 100 to 600 m$^2$/g. In this context, the iron complex V is preferably applied in an amount such that the concentration of the iron from the iron complex V in the finished catalyst system is 1 to 100 µmol, preferably 5 to 80 µmol, and particularly preferably 10 to 60 µmol per g of finished catalyst system.

The catalyst system can also additionally comprise as a further component one or more metal compounds of group 1, 2 or 13 of the periodic table, in particular metal compounds of the general formula (XX)

$$M^G(R^{1G})_{r^G}(R^{2G})_{s^G}(R^{3G})_{t^G} \quad (XX)$$

in which $M^G$ denotes Li, Na, K, Be, Mg, Ca, Sr, Ba, boron, aluminum, gallium, indium, thallium or zinc, in particular Li, Na, K, Mg, boron, aluminum or Zn, $R^{1G}$ denotes hydrogen or $C_1$-$C_{10}$-alkyl, $C_6$-$C_{15}$-aryl, alkylaryl or arylalkyl having in each case 1 to 10 C atoms in the alkyl radical and 6 to 20 C atoms in the aryl radical, $R^{2G}$ and $R^{3G}$ denote hydrogen, halogen, $C_1$-$C_{10}$-alkyl, $C_6$-$C_{15}$-aryl, alkylaryl, arylalkyl or alkoxy having in each case 1 to 20 C atoms in the alkyl radical and 6 to 20 C atoms in the aryl radical, or alkoxy with $C_1$-$C_{10}$-alkyl or $C_6$-$C_{15}$-aryl, $r^G$ denotes an integer from 1 to 3 and $s^G$ and $t^G$ denote integers from 0 to 2, wherein the sum $r^G+s^G+t^G$ corresponds to the valency of $M^G$, wherein the metal compounds of the formula (XX) conventionally are not identical to the activator. Mixtures of various metal compounds of the formula (XX) can also be employed.

Preferred metal compounds of the general formula (XX) are those in which $M^G$ denotes lithium, magnesium, boron or aluminum and $R^{1G}$ represents $C_1$-$C_{20}$-alkyl.

Particularly preferred metal compounds of the formula (XX) are methyllithium, ethyllithium, n-butyllithium, methylmagnesium chloride, methylmagnesium bromide, ethylmagnesium chloride, ethylmagnesium bromide, butylmagnesium chloride, dimethylmagnesium, diethylmagnesium, dibutylmagnesium, n-butyl-n-octylmagnesium, n-butyl-n-heptylmagnesium, in particular n-butyl-n-octylmagnesium, tri-n-hexyl-aluminum, triisobutylaluminum, tri-n-butylaluminum, triethylaluminum, dimethylaluminum chloride, dimethylaluminum fluoride, methylaluminum dichloride, methylaluminum sesquichloride, diethylaluminum chloride and trimethylaluminum and mixtures thereof. The partial hydrolysis products of aluminum-alkyls with alcohols can also be employed.

If a metal compound (XX) is employed, the catalyst system preferably comprises this in an amount such that the molar ratio of MG from formula (XX) to iron from the iron complex V is from 3000:1 to 0.1:1, preferably from 800:1 to 0.2:1, and particularly preferably from 100:1 to 1:1.

As a rule, the metal compound of the general formula (XX) is employed as a constituent of a catalyst system for the polymerization or copolymerization of olefins. In this context, the metal compound (XX) can be used, for example, for the preparation of a catalyst solid comprising the support and/or added during or shortly before the polymerization. In this context, the metal compounds (XX) used can be identical or different. It is also possible, especially if the catalyst solid comprises no activating component, for the catalyst system to comprise one or more activators, in addition to the catalyst solid, which are identical to or different from compounds (XX) possibly contained in the catalyst solid.

The metal compound (XX) can likewise be reacted with the iron complex V and optionally the activator and support in any desired sequence. For example, the iron complex V can be brought into contact with the activator or activators and/or the support either before or after being brought into contact with the olefins to be polymerized. Preactivation with one or more activators before thorough mixing with the olefin and further addition of the same or other activators and/or the support after this mixture has been brought into contact with the olefin is also possible. A preactivation is as a rule carried out at temperatures of between 10-100° C., preferably between 20-80° C.

In another preferred embodiment, a catalyst solid is prepared from an iron complex V, an activator and a support, as described above, and this is brought into contact with the metal compound (XX) during, at the start of or shortly before the polymerization. Preferably, the metal compound (XX) is first brought into contact with the α-olefin to be polymerized and the catalyst solid of an iron complex V, an activator and a support is then added as described above.

In a further preferred embodiment, the support is first brought into contact with the metal compound (XX) and thereafter the procedure with the iron complex V and possibly further activator is as above.

The catalyst system can optionally comprise further catalysts which are suitable for olefin polymerization. Possible catalysts here are, in particular, conventional Ziegler-Natta catalysts based on titanium, conventional Phillips catalysts based on chromium compounds, in particular chromium oxides, metallocenes, nickel and palladium bisimine systems (for the preparation thereof see WO-A-98/03559) and cobalt pyridinebisimine compounds (for the preparation thereof see WO-A-98/27124).

So-called Ziegler catalyst components (as described e.g. in Falbe, J.; Regitz, M. (ed.); Römpp Chemie Lexi-kon [Römpp Chemical Dictionary]; 9th ed.; Thieme; 1992; New York; vol.

6, p. 5128-5129) and/or metallocene catalyst components are preferred. Metallocene catalyst components are particularly preferred.

The Ziegler catalyst component is preferably a compound of a metal of group IVa (e.g. titanium, zirconium or hafnium), Va (e.g. vanadium or niobium) or VIa (e.g. chromium or molybdenum) of the periodic table of the elements. Halides, oxides, oxyhalides, hydroxides or alkoxides are preferred. Examples of Ziegler catalyst components which are given by way of example but are not limiting are: titanium tetrachloride, zirconium tetrachloride, hafnium tetrachloride, titanium trichloride, vanadium trichloride, vanadium oxychloride, chromium trichloride or chromium oxide.

In the present application, metallocene catalyst components are understood as meaning cyclopentadienyl complexes which comprise one, two or three cyclopentadienyl ligands. In the present application, cyclopentadienyl ligand is understood as meaning any system which comprises a cyclic 5-membered ring system having 6 n electrons, such as, for example, indenyl or fluorenyl systems. Metallocene complexes of metals of group III and the lanthanoid group (e.g. lanthanum or yttrium) as well as metals of group IV (e.g. titanium, zirconium or hafnium), V (e.g. vanadium or niobium) or VI of the periodic table of the elements (e.g. chromium or molybdenum) are preferred, and cyclopentadienyl complexes of titanium, zirconium or hafnium are particularly preferred. The cyclopentadienyl complexes can be e.g. bridged or non-bridged dicyclopentadienyl complexes, such as are described e.g. in EP 129 368, EP 561 479, EP 545 304 and EP 576 970, or monocyclopentadienyl complexes, such as bridged amidocyclopentadienyl complexes which are described e.g. in EP 416 815.

The molar ratio of iron complex V to olefin polymerization catalyst is conventionally in the range of from 1:100 to 100:1, preferably from 1:10 to 10:1, and particularly preferably from 1:5 to 5:1.

It is furthermore possible first to prepolymerize the catalyst system with α-olefins, preferably linear $C_2$-$C_{10}$-1-alkenes, and in particular with ethylene or propylene, and then to use the resulting prepolymerized catalyst solid in the actual polymerization. The weight ratio of catalyst solid employed in the prepolymerization to monomer to be polymerized in is conventionally in the range of from 1:0.1 to 1:1000, preferably 1:1 to 1:200.

A small amount of an olefin, preferably an α-olefin, for example vinylcyclohexane, styrene or phenyldimethylvinylsilane, as a modifying component, an antistatic or a suitable inert compound, such as a wax or oil, can furthermore be added as an additive during or after the preparation of the catalyst system. In this context, the molar ratio of additives to iron complex V is conventionally in the range of from 1:1000 to 1000:1, preferably from 1:5 to 20:1.

The catalyst composition according to the invention or the catalyst system is suitable for the preparation of the polyethylene according to the invention, which has advantageous use and processing properties.

For the preparation of the polyethylene according to the invention, ethylene is polymerized with α-olefins having 3 to 12 C atoms as described above.

In the process according to the invention for the polymerization, ethylene is polymerized with α-olefins having 3 to 12 C atoms. Preferred α-olefins are linear or branched $C_2$-$C_{12}$-1-alkenes, in particular linear $C_2$-$C_{10}$-1-alkenes, such as ethene, propene, 1-butene, 1-pentene, 1-hexene, 1-heptene, 1-octene or 1-decene, or branched $C_2$-$C_{10}$-1-alkenes, such as 4-methyl-1-pentene. $C_4$-$C_{12}$-1-Alkenes, in particular linear $C_6$-$C_{10}$-1-alkenes, are particularly preferred. Mixtures of various α-olefins can also be polymerized. Preferably, at least one α-olefin chosen from the group consisting of ethene, propene, 1-butene, 1-pentene, 1-hexene, 1-heptene, 1-octene and 1-decene is polymerized. Monomer mixtures with at least 50 mol % of ethene are preferably used.

The process according to the invention for the polymerization of ethylene with α-olefins can be carried out with all the industrially known polymerization processes at temperatures in the range of from −60 to 350° C., preferably from 0 to 200° C., and particularly preferably from 25 to 150° C., and under pressures of from 0.5 to 4000 bar, preferably 1 to 100 bar, and particularly preferably from 3 to 40 bar. The polymerization can be carried out in a known manner in bulk, in suspension, in the gas phase or in a supercritical medium in the conventional reactors used for the polymerization of olefins. It can be carried out discontinuously or, preferably, continuously in one or more stages. High pressure polymerization processes in tube reactors or autoclaves, solution processes, suspension processes, stirred gas phase processes or gas phase fluidized bed processes are possible.

The polymerizations are conventionally carried out at temperatures in the range of from −60 to 350° C., preferably in the range of from 20 to 300° C. and under pressures of from 0.5 to 4000 bar. The mean dwell times are conventionally from 0.5 to 5 hours, preferably from 0.5 to 3 hours. The advantageous pressure and temperature ranges for carrying out the polymerizations conventionally depend on the polymerization method. In the high pressure polymerization processes, which are conventionally carried out at pressures of between 1000 and 4000 bar, in particular between 2000 and 3500 bar, as a rule high polymerization temperatures are also established. Advantageous temperature ranges for these high pressure polymerization processes are between 200 and 320° C., in particular between 220 and 290° C. In low pressure polymerization processes, as a rule a temperature which is at least a few degrees below the softening temperature of the polymer is established. In particular, temperatures of between 50 and 180° C., preferably between 70 and 120° C. are established in these polymerization processes. In the suspension polymerizations, the polymerization is conventionally carried out in a suspending agent, preferably in an inert hydrocarbon, such as, for example, isobutane, or mixtures of hydrocarbons, or in the monomers themselves. The polymerization temperatures are in general in the range of from −20 to 115° C., and the pressure is in general in the range of from 1 to 100 bar. The solids content of the suspension is in general in the range of from 10 to 80%. The process can be carried out either discontinuously, e.g. in stirred autoclaves, or continuously, e.g. in tube reactors, preferably in loop reactors. In particular, the polymerization can be carried out by the Phillips-PF process, as described in U.S. Pat. No. 3,242,150 and U.S. Pat. No. 3,248,179. The gas phase polymerization is in general carried out in the range of from 30 to 125° C. at pressures of from 1 to 50 bar.

Of the polymerization processes mentioned, gas phase polymerization, in particular in gas phase fluidized bed reactors, solution polymerization, and suspension polymerization, in particular in loop and stirred tank reactors, are particularly preferred. The gas phase polymerization can also be carried out in the so-called condensed or supercondensed procedure, in which some of the circulating gas is cooled to below the dew point and is recycled into the reactor as a two-phase mixture. A so-called multizone reactor in which two polymerization zones are linked to one another and the polymer is passed in alternation several times through these two zones, it also being possible for the two zones to have different polymerization conditions, can furthermore be employed. Such a reactor is described, for example, in WO 97/04015. The different or also identical polymerization processes can also optionally be connected to one another in series and in this way form a polymerization cascade, such as, for example, in the Hostalen® process. A parallel reactor program of two or more identical or different processes is also possible. Molar mass regulators, for example hydrogen, or conventional additives, such as antistatics, can furthermore also be co-used in the polymerizations. Preferably, in order to obtain the high contents of vinyl groups, the polymerization is carried out in the absence of hydrogen.

The polymerization is preferably carried out in an individual reactor, in particular in a gas phase reactor.

The unsymmetric complexes according to the invention are very active in the polymerization of ethylene. Their activity is higher than that of the corresponding symmetric complexes. They are furthermore distinguished by narrow molar mass distributions.

A further advantage is that the process is also very particularly suitable for the preparation of commercial amounts. Amounts of 2-200 kg of the bisimine compound can be prepared without problems. Furthermore, the bisimine product is formed in high purities, so that further working up steps are no longer necessary.

The following experiment examples serve to further illustrate the invention, without it thereby being intended to limit the scope of the invention.

EXAMPLES

Example 1

Preparation of 1-{6-[1-(2-chloro-4,6-dimethylphenylimino)ethyl]pyridin-2-yl}ethanone in heptane

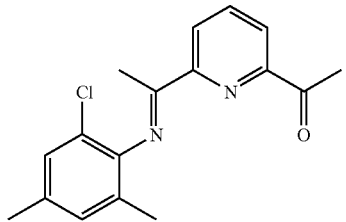

20 g of 2,6-diacetylpyridine (0.123 mol), 19.08 g of 2-chloro-4,6-dimethylaniline (0.123 mol) and 0.5 g of p-toluenesulfonic acid were heated under reflux on a water separator in 500 ml of heptane for 75 min. The insoluble solid was filtered off. The solvent was distilled off from the filtrate down to 150 ml, and the remaining filtrate was cooled to room temperature, while stirring. 25.3 g of a yellow solid precipitated out. This was filtered off and recrystallized from 60 ml of hot isopropanol. A total of 12.9 g (0.043 mol) of 1-{6-[1-(2-chloro-4,6-dimethylphenylimino)ethyl]-pyridin-2-yl}ethanone were obtained in a yield of 35%.

The GC/MS showed a purity of the product of greater than 99%.

Comparison Example V1

Preparation of 1-{6-[1-(2-chloro-4,6-dimethylphenylimino)ethyl]pyridin-2-yl}ethanone in toluene 10 g of 2,6-diacetylpyridine (0.0613 mol), 9.54 g of 2-chloro-4,6-dimethylaniline (0.0613 mol) and 0.6 g of p-toluenesulfonic acid were heated under reflux on a water separator in 400 ml of toluene for 90 min. The solvent was distilled off completely and the residue was recrystallized from 50 ml of isopropanol. 5.66 g (0.019 mol) of 1-{6-[1-(2-chloro-4,6-dimethyl-phenylimino)ethyl]pyridin-2-yl}ethanone were obtained in a yield of 31%.

The GC/MS showed a purity of the product of greater than 96%.

Comparison Example V2

Preparation of 1-{6-[1-(2-chloro-4,6-dimethylphenylimino)ethyl]pyridin-2-yl}ethanone in methanol 10 g of 2,6-diacetylpyridine (0.0613 mol), 9.54 g of 2-chloro-4,6-dimethylaniline (0.0613 mol) and 0.6 g of p-toluenesulfonic acid were heated under reflux on a water separator in 400 ml of methanol for 90 min. The solvent was distilled off completely and the residue was recrystallized twice from 50 ml of isopropanol. 0.92 g (0.0031 mol) of 1-{6-[1-(2-chloro-4,6-dimethyl-phenylimino)ethyl]pyridin-2-yl}ethanone was obtained in a yield of 5%.

The GC/MS showed a purity of the product of 72%.

Example 2

Preparation of 1-{6-[1-(2,6-diethylphenylimino)-ethyl]pyridin-2-yl}ethanone

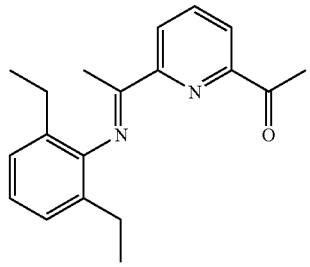

10.35 g of 2,6-diacetylpyridine (0.0634 mol), 7.10 g of 2,6-diethylaniline (0.0476 mol) and 2 ml of formic acid were stirred in 300 ml of heptane at room temperature for 71 h. The insoluble solid was filtered off (11.10 g) and dissolved in 150 ml of toluene and the solution was extracted with 10 ml of a saturated Na$_2$CO$_3$ solution. The toluene phase was dried over Na$_2$SO$_4$ and filtered and the solvent was distilled off in vacuo. 5.58 g (0.0198 mol) of the product were obtained in a purity of 99% (GC/MS) in a yield of 40%. The mother liquor of the reaction solution was freed completely from the solvent and the residue was recrystallized from hot heptane. 2.00 g (0.0068 mol) of the product were additionally obtained in a purity of 100% (GC/MS). The total yield was 54%.

Example 3

Preparation of 2-[1-(2-chloro-4,6-dimethylphenylimino)ethyl]-6-[1-(2,6-diethylphenyl-imino)ethyl]pyridine

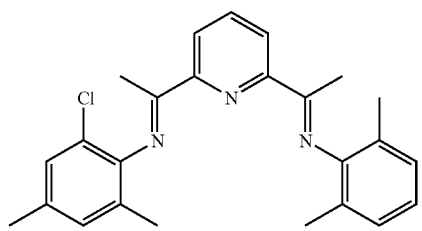

18.80 g of 1-{6-[1-(2-chloro-4,6-dimethylphenylimino)-ethyl]pyridin-2-yl}ethanone (0.0625 mol), 15.13 g of 2,6-dimethylaniline (0.125 mol) and 20.0 g of Sicapent were heated under reflux under argon in 300 ml of tetrahydrofuran for 17 h. A further portion of Sicapent (10.0 g) was added and the mixture was heated under argon for a further 4 h and then cooled to room temperature. It was filtered and the residue on the filter was washed with 50 ml of tetrahydrofuran. The solvent was distilled off completely from the combined filtrates and the residue was stirred with 50 ml of methanol. The precipitate formed was filtered off, washed twice with methanol, stirred with 100 ml of hot methanol and then filtered. 16.92 g (0.0419 mol) of 2-[1-(2-chloro-4,6-dimethylphenylimino)ethyl]-6-[1-(2,6-dimethylphenylimino)ethyl]pyridine were obtained in a yield of 67%.

$^1$H-NMR (300 MHz) in CDCl$_3$: δ=2.07 (s, 6H), 2.09 (s, 6H), 2.26 (s, 3H), 2.32 (s, 6H), 6.97 (m, 2H), 7.07-7.15 (3H), 7.93 (t, 1H), 8.50 (m, 2H)

$^{13}$C-NMR: δ=16.78, 17.25, 18.28, 18.57, 20.90, 122.49, 122.58, 122.78, 122.91, 123.11, 123.34, 125.70, 127.81, 128.21, 128.57, 129.82, 133.90, 137.24, 144.57, 149.03, 155.14, 155.43, 167.49, 169.88

Example 4

Preparation of 2-[1-(2-chloro-4,6-dimethylphenylimino)ethyl]-6-[1-(2,6-diethylphenyl-imino)ethyl]pyridine

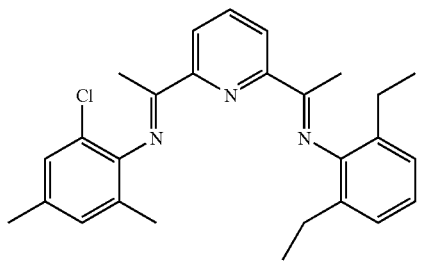

1.00 g of 1-{6-[1-(2-chloro-4,6-dimethylphenylimino)-ethyl]pyridin-2-yl}ethanone (3.3 mol), 0.99 g of 2,6-diethylaniline (6.6 mmol) and 1.0 g of Sicapent were heated under reflux under argon in 50 ml of tetrahydrofuran for 2 h. A further portion of Sicapent (0.5 g) was added and the mixture was heated under reflux under argon for a further 1.5 h. A further portion of Sicapent (0.5 g) and 0.50 g of 2,6-diethylaniline (3.3 mmol) were added and the mixture was heated under reflux under argon for a further 15 h and then cooled to room temperature. The reaction mixture was filtered and the residue on the filter was washed with 10 ml of tetrahydrofuran. The filtrate was topped up to 125 ml with tetrahydrofuran, 4 g of Sicapent were added and the mixture was heated again under reflux under argon for 2.5 h and then cooled to room temperature. It was filtered and the residue on the filter was washed with 10 ml of tetrahydrofuran. The solvent was then distilled off completely and the residue was stirred with 10 ml of methanol. The precipitate formed was filtered off and washed twice with methanol. After drying in vacuo, 0.36 g (0.8 mmol) of 2-[1-(2-chloro-4,6-dimethylphenylimino)ethyl]-6-[1-(2,6-diethylphenylimino)ethyl]pyridine was obtained in a yield of 25%.

Example 5

Preparation of 2-[1-(2-chloro-4,6-dimethylphenylimino)ethyl]-6-[1-(2,6-diisopropylphenyl-imino)ethyl]pyridine

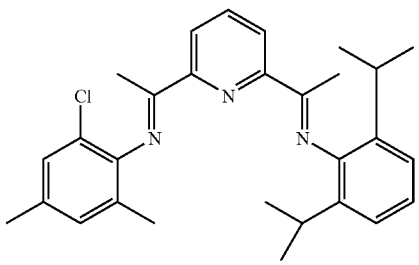

18.80 g of 1-{6-[1-(2-chloro-4,6-dimethylphenylimino)-ethyl]pyridin-2-yl}ethanone (0.0625 mol), 22.16 g of 2,6-diisopropylaniline (0.125 mol) and 20.0 g of Sicapent were heated under reflux under argon in 300 ml of tetrahydrofuran for 17 h. A further portion of Sicapent (10.0 g) was added and the mixture was heated under argon for a further 4 h and then cooled to room temperature. It was filtered and the residue on the filter was washed with 50 ml of tetrahydrofuran. The solvent was distilled off completely from the combined filtrates and the residue was stirred with 50 ml of methanol. The precipitate formed was filtered off, washed twice with methanol, stirred with 100 ml of hot methanol and then filtered. 17.84 g (0.0388 mol) of 2-[1-(2-chloro-4,6-dimethylphenylimino)ethyl]-6-[1-(2,6-diisopropylphenylimino)ethyl]pyridine were obtained in a yield of 62%.

Example 6

Preparation of 2-[1-(2-chloro-4,6-dimethylphenylimino)ethyl]-6-[1-(2,6-dimethylphenyl-imino)ethyl]pyridineiron(II) chloride

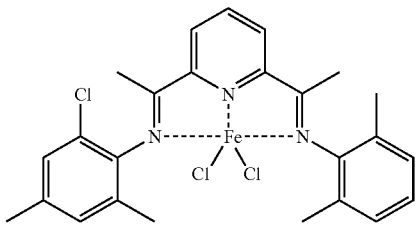

850 mg (2.104 mmol) of 2-[1-(2-chloro-4,6-dimethylphenylimino)ethyl]-6-[1-(2,6-dimethylphenyl-imino)ethyl]pyridine were suspended in 20 ml of n-butanol, and a solution of 267 mg of iron(II) chloride (2.104 mmol) in 40 ml of n-butanol was added at room temperature, while stirring. The suspension was heated at 80° C. for 2 h and then stirred at room temperature for 14 h. The butanol was distilled off under a high vacuum and the residue obtained in this way was washed three times with diethyl ether. The solid obtained in this way was dried under a high vacuum for 8 h. 1.005 g of 2-[1-(2-chloro-4,6-dimethylphenylimino)ethyl]-6-[1-(2,6-dimethylphenylimino)ethyl]pyridineiron(II) chloride were obtained in a yield of 90%. Decomposition point: 220° C.

Example 7

Preparation of 2-[1-(2-chloro-4,6-dimethylphenyl-imino)ethyl]-6-[1-(2,6-diethylphenylimino)-ethyl]pyridineiron(II) chloride

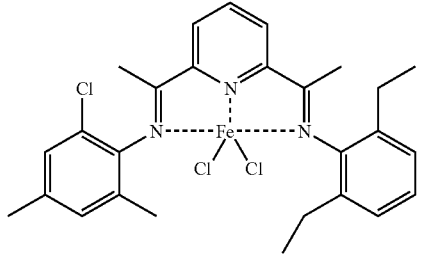

0.36 g of 2-[1-(2-chloro-4,6-dimethylphenylimino)-ethyl]-6-[1-(2,6-diethylphenylimino)ethyl]pyridine (0.8 mmol) was dissolved in 10 ml of tetrahydrofuran, and 0.15 g of $FeCl_2.4H_2O$ (0.8 mmol) was added at room temperature, while stirring. A precipitate formed, and was isolated by filtration after 1 h. It was washed twice with tetrahydrofuran and the 2-[1-(2-chloro-4,6-dimethylphenylimino)ethyl]-6-[1-(2,6-diethylphenyl-imino)ethyl]pyridineiron(II) chloride was freed from solvent residues under reduced pressure. 0.30 g (0.5 mmol) was obtained in a yield of 63%.

Example 8

Preparation of 2-[1-(2-chloro-4,6-dimethylphenyl-imino)ethyl]-6-[1-(2,6-diisopropylphenylimino)-ethyl]pyridineiron(II) chloride

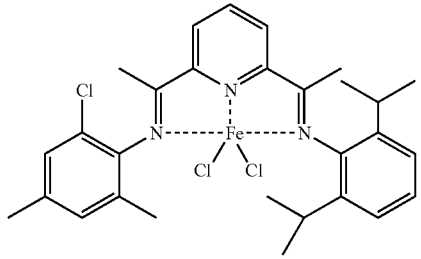

0.32 g of 2-[1-(2-chloro-4,6-dimethylphenylimino)ethyl]-6-[1-(2,6-diisopropylphenylimino)ethyl]pyridine (0.70 mmol) was dissolved in 10 ml of tetrahydrofuran, and 0.14 g of $FeCl_2.4H_2O$ (0.68 mmol) was added at room temperature, while stirring. A precipitate formed, and was isolated by filtration after 1 h and washed twice with tetrahydrofuran. The product 2-[1-(2-chloro-4,6-dimethylphenylimino)ethyl]-6-[1-(2,6-diisopropylphenyl-imino)ethyl]pyridineiron(II) chloride obtained in this way was freed from solvent residues under reduced pressure. 0.38 g (0.65 mmol) was obtained in a yield of 95%.

Comparison Example V3

2,6-Bis[1-(2,6-dimethylphenylimino)ethyl]pyridine-iron(II) chloride was prepared in accordance with Lutz et al., C. R. Chimie 5 (2002), p. 43-48.

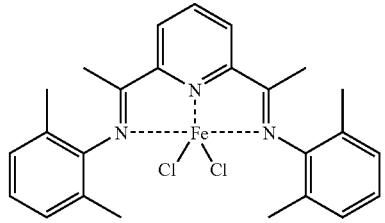

Comparison Example V4

2,6-Bis[1-(2-chloro-4,6-dimethylphenylimino)ethyl]-pyridineiron(II) chloride was prepared in accordance with Lutz et al., C. R. Chimie 5 (2002), p. 43-48.

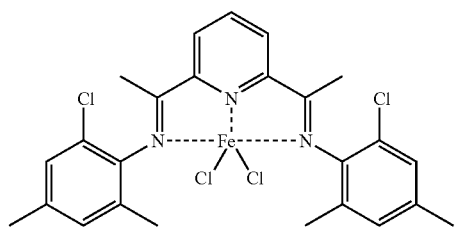

Comparison Example V5

2,6-Bis[1-(2,6-diisopropylphenylimino)ethyl]pyri-dine-iron(II) chloride was prepared in accordance with WO9912981, Ex. 1.

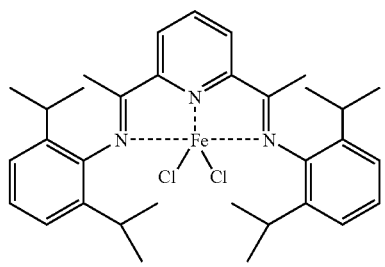

Polymerization

The polymerization experiments were carried out in a 1-l four-necked flask provided with a contact thermometer, Teflon blade stirrer, gas inlet tube, condenser and heating mantle. 250 ml of toluene were initially introduced into this flask and the corresponding amounts of the complex were added at 40° C. under argon (see Table 1). The solution was then heated at 75° C. for 10 min. Thereafter, it was cooled again to 40° C. and the amount of 30% strength methylalu-moxane solution (MAO) in toluene from Crompton stated in Table 1 was added. Thereafter, 20 to 40 l/h of ethylene were passed through this solution.

To end the polymerization, the ethylene feed was stopped and argon was passed through the solution. A mixture of 15 ml of concentrated hydrochloric acid and 50 ml of methanol was then added and, after stirring for 15 min, a further 250 ml of methanol were added, the polymer formed precipitating out completely. The polymer was filtered off over a glass filter frit, washed three times with methanol and dried at 70° C. in vacuo. The polymerization and product data are summarized in Table 1.

TABLE 1

| Ex. | Complex from Ex. | Amount of complex [µmol] | Complex:Al | t-(Poly) [min] | Polymer [g] | Activity [g of PE/(mmol · h)] | η [dl/g] | $M_w$ [g/mol] | $M_w/M_n$ |
|---|---|---|---|---|---|---|---|---|---|
| 9 | 6 | 23.3 | 1:500 | 20 | 17.6 | 2269 | 0.852 | 134,885 | 4.79 |
| V6 | V3 | 18.8 | 1:500 | 12 | 7.8 | 2079 | 0.59 | 27,300 | 6.59 |
| V7 | V4 | 22.0 | 1:500 | 15 | 10.44 | 1901 | 0.523 | 23,150 | 10.1 |

The determination of the molar mass distributions and the means Mn, Mw, and Mw/Mn derived therefrom was carried out by means of high temperature gel permeation chromatography in accordance with DIN 55672 on a WATERS 150 C with the following columns connected in series: 3× SHODEX AT 806 MS, 1× SHODEX UT 807 and 1× SHODEX AT-G under the following conditions: solvent: 1,2,4-trichlorobenzene (stabilized with 0.025 wt. % of 2,6-di-tert-butyl-4-methylphenol), flow rate: 1 ml/min, 500 µl injection volume, temperature: 135° C., calibration with PE standards. The evaluation was carried out with WIN-GPC.

The Staudinger index (η)[dl/g] was determined with an automated Ubbelohde viscometer (Lauda PVS 1) with decalin as the solvent at 130° C. (ISO1628 at 130° C., 0.001 g/ml of decalin).

The unsymmetric complex according to the invention from Ex. 6 shows higher activities and molar masses than the two corresponding symmetric complexes from V3 and V4. At the same time, the molar mass distribution is narrower.

Example 10

21.1 µmol of the complex from Example 7, 2-[1-(2-chloro-4,6-dimethylphenylimino)ethyl]-6-[1-(2,6-diethylphenylimino)ethyl]pyridineiron(II) chloride, was used for ethylene polymerization as described above, with a molar ratio of Fe from the complex to Al from the MAO of 1:500. The polymerization was interrupted after 20 min. The activity of the complex was 2786 g of PE/(mmol of complex·h). The polyethylene obtained had a viscosity η of 0.807 dl/g.

Example 11

12.1 µmol of the complex from Example 8, 2-[1-(2-chloro-4,6-dimethylphenylimino)ethyl]-6-[1-(2,6-diisopropylphenylimino)ethyl]pyridineiron(II) chloride, was used for ethylene polymerization as described above, with a molar ratio of Fe from the complex to Al from the MAO of 1:500. The polymerization was interrupted after 10 min. The activity of the complex was 6843 g of PE/(mmol of complex·h).

Comparison Example 8

14.1 µmol of the complex from Comparison Example V5, 2,6-bis[1-(2,6-diisopropylphenylimino)ethyl]pyridine-iron (II) chloride, was used for ethylene polymerization as described above, with a molar ratio of Fe from the complex to Al from the MAO of 1:500. The polymerization was interrupted after 20 min. The activity of the complex was 976 g of PE/(mmol of complex·h).

The invention claimed is:
1. An unsymmetric iron complex of the formula V,

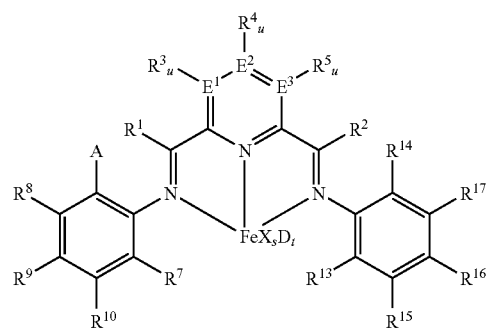

wherein:
A is chlorine, bromine, iodine, $CF_3$ or $OR^{11}$,
each of $R^1$ and $R^2$ is independently hydrogen, $C_1$-$C_{22}$-alkyl, $C_2$-$C_{22}$-alkenyl, $C_6$-$C_{22}$-aryl, arylalkyl having 1 to 10 carbon atoms in the alkyl radical and 6-20 carbon atoms in the aryl radical, or five-, six- or seven-membered heterocyclyl comprising at least one atom selected from the group consisting of N, P, O and S;
wherein $R^1$ and $R^2$ are optionally substituted by halogens, $NR^{11}_2$, $OR^{11}$ or $SiR^{12}_3$; and
wherein $R^1$ optionally bonds with $R^3$, and $R^2$ optionally bonds with $R^5$, in each case to form a five-, six- or seven-membered ring,
$R^7$ is a $C_1$-$C_{20}$ alkyl;
each of $R^3$-$R^5$, $R^8$-$R^{10}$, and $R^{15}$-$R^{17}$ is independently hydrogen, $C_1$-$C_{22}$-alkyl, $C_2$-$C_{22}$-alkenyl, $C_6$-$C_{22}$-aryl, arylalkyl having 1 to 10 carbon atoms in the alkyl radical and 6-20 carbon atoms in the aryl radical, $NR^{11}_2$, $OR^{11}$, halogen, $SiR^{12}_3$ or five-, six- or seven-membered heterocyclyl comprising at least one atom selected from the group consisting of N, P, O and S;
wherein $R^3$-$R^5$, $R^7$-$R^{10}$, and $R^{15}$-$R^{17}$ are optionally substituted by halogens, $NR^{11}_2$, $OR^{11}$ or $SiR^{12}_3$; and
wherein $R^3$ optionally bonds with $R^4$, $R^4$ optionally bonds with $R^5$, $R^7$ optionally bonds with $R^{10}$, $R^{10}$ bonds with $R^9$, $R^9$ optionally bonds with $R^8$, $R^{17}$ optionally bonds with $R^{16}$, and $R^{16}$ optionally bonds with $R^{15}$, in each case to form a five-, six- or seven-membered carbocyclic or heterocyclic ring, the heterocyclic ring comprising at least one atom from the group consisting of N, P, O and S,
each of $R^{13}$ and $R^{14}$ is independently $C_1$-$C_{20}$-alkyl bonded with the aryl ring via a primary or secondary carbon atom,
each $R^{11}$ is independently hydrogen, $C_1$-$C_{22}$-alkyl, $C_2$-$C_{22}$-alkenyl, $C_6$-$C_{22}$-aryl, arylalkyl having 1 to 10 carbon atoms in the alkyl radical and 6-20 carbon atoms in the aryl radical or $SiR^{12}_3$, wherein $R^{11}$ is optionally substituted by halogens and two $R^{11}$ radicals optionally bond to form a five- or six-membered ring, each $R^{12}$ is independently hydrogen, $C_1$-$C_{22}$-alkyl, $C_2$-$C_{22}$-alkenyl, $C_6$-$C_{22}$-aryl or arylalkyl having 1 to 10 carbon atoms in the alkyl radical and 6-20 carbon atoms in the aryl radical and two $R^{12}$ radicals optionally bond to form a five- or six-membered ring, each of $E^1$-$E^3$ is independently carbon, nitrogen or phosphorus, each u is independently 0 for $E^1$-$E^3$ as nitrogen or phosphorus and 1 for $E^1$-$E^3$ as carbon, each X is independently fluorine, chlorine, bromine, iodine, hydrogen, $C_1$-$C_{20}$-alkyl, $C_2$-$C_{10}$-alkenyl, $C_6$-$C_{20}$-aryl, arylalkyl having 1-10 carbon atoms in the alkyl radical and 6-20 carbon atoms in the aryl radical, $NR^{18}{}_2$, $OR^{18}$, $SR^{18}$, $SO_3R^{18}$, $OC(O)R^{18}$, CN, SCN, β-diketonate, CO, $BF_4{}^-$, $PF_6{}^-$ or bulky non-coordinating anions, and the radicals X can be bonded with one another, each $R^{18}$ is independently hydrogen, $C_1$-$C_{20}$-alkyl, $C_2$-$C_{20}$-alkenyl, $C_6$-$C_{20}$-aryl, arylalkyl having 1 to 10 carbon atoms in the alkyl radical and 6-20 carbon atoms in the aryl radical or $SiR^{19}{}_3$, wherein $R^{18}$ can be substituted by halogens or nitrogen- or oxygen-containing groups and two $R^{18}$ radicals optionally bond to form a five- or six-membered ring, each $R^{19}$ is independently hydrogen, $C_1$-$C_{20}$-alkyl, $C_2$-$C_{20}$-alkenyl, $C_6$-$C_{20}$-aryl or arylalkyl having 1 to 10 carbon atoms in the alkyl radical and 6-20 carbon atoms in the aryl radical, wherein $R^{19}$ can be substituted by halogens or nitrogen- or oxygen-containing groups and two $R^{19}$ radicals optionally bond to form a five- or six-membered ring, s is 1, 2, or 3, D is a neutral donor, and t is 0 to 2.

2. A catalyst system comprising at least one iron complex of claim 1, one or more activators, optionally an organic or inorganic support, optionally further catalysts suitable for olefin polymerization and optionally one or more Group 1, 2, or 13 metal compounds.

3. A process which comprises polymerizing one or more olefins in the presence of the catalyst system of claim 2.

4. A prepolymerized catalyst system comprising the catalyst system of claim 2 and, polymerized into this, one or more linear $C_2$-$C_{10}$-1-alkenes in a weight ratio of from 1:0.1 to 1:1000, based on the amount of catalyst system.

5. A process which comprises polymerizing one or more olefins in the presence of the iron complex of claim 1.

6. An unsymmetric bis(imino) compound of the formula IV,

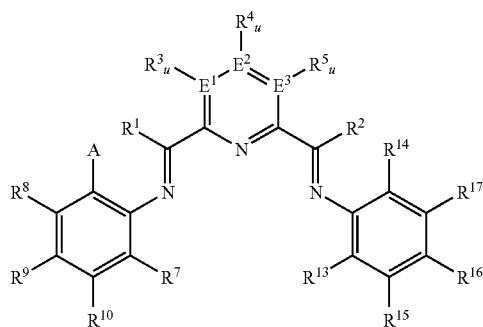

wherein:

A is chlorine, bromine, iodine, $CF_3$ or $OR^{11}$, each of $R^1$ and $R^2$ is independently hydrogen, $C_1$-$C_{22}$-alkyl, $C_2$-$C_{22}$-alkenyl, $C_6$-$C_{22}$-aryl, arylalkyl having 1 to 10 carbon atoms in the alkyl radical and 6-20 carbon atoms in the aryl radical, or five-, six- or seven-membered heterocyclyl comprising at least one atom selected from the group consisting of N, P, O and S;

wherein $R^1$ and $R^2$ are optionally substituted by halogens, $NR^{11}{}_2$, $OR^{11}$ or $SiR^{12}{}_3$; and wherein $R^1$ optionally bonds with $R^3$, and $R^2$ optionally bonds with $R^5$, in each case to form a five-, six- or seven-membered ring, $R^7$ is a $C_1$-$C_{20}$-alkyl;

each of $R^3$-$R^5$, $R^8$-$R^{10}$, and $R^{15}$-$R^{17}$ is independently hydrogen, $C_1$-$C_{22}$-alkyl, $C_2$-$C_{22}$-alkenyl, $C_6$-$C_{22}$-aryl, arylalkyl having 1 to 10 carbon atoms in the alkyl radical and 6-20 carbon atoms in the aryl radical, $NR^{11}{}_2$, $OR^{11}$, halogen, $SiR^{12}{}_3$ or five-, six- or seven-membered heterocyclyl comprising at least one atom selected from the group consisting of N, P, O and S;

wherein $R^3$-$R^5$, $R^7$-$R^{10}$, and $R^{15}$-$R^{17}$ are optionally substituted by halogens, $NR^{11}{}_2$, $OR^{11}$ or $SiR^{12}{}_3$; and wherein $R^3$ optionally bonds with $R^4$, $R^4$ optionally bonds with $R^5$, $R^7$ optionally bonds with $R^{10}$, $R^{10}$ bonds with $R^9$, $R^9$ optionally bonds with $R^8$, $R^{17}$ optionally bonds with $R^{16}$, and $R^{16}$ optionally bonds with $R^{15}$, in each case to form a five-, six- or seven-membered carbocyclic or heterocyclic ring, the heterocyclic ring comprising at least one atom selected from the group consisting of N, P, O and S, each of $R^{13}$ and $R^{14}$ is independently $C_1$-$C_{20}$-alkyl bonded with the aryl ring via a primary or secondary carbon atom, each $R^{11}$ is independently hydrogen, $C_1$-$C_{22}$-alkyl, $C_2$-$C_{22}$-alkenyl, $C_6$-$C_{22}$-aryl, arylalkyl having 1 to 10 carbon atoms in the alkyl radical and 6-20 carbon atoms in the aryl radical or $SiR^{12}{}_3$, wherein $R^{11}$ is optionally substituted by halogens and two $R^{11}$ radicals optionally bond to form a five- or six-membered ring, each $R^{12}$ is independently hydrogen, $C_1$-$C_{22}$-alkyl, $C_2$-$C_{22}$-alkenyl, $C_6$-$C_{22}$-aryl or arylalkyl having 1 to 10 carbon atoms in the alkyl radical and 6-20 carbon atoms in the aryl radical and two $R^{12}$ radicals optionally bond to form a five- or six-membered ring, each of $E^1$-$E^3$ is independently carbon, nitrogen or phosphorus, and each u is independently 0 for $E^1$-$E^3$ as nitrogen or phosphorus and 1 for $E^1$-$E^3$ as carbon.

7. The bis(imino) compound of claim 6 wherein each of $E^1$-$E^3$ is carbon.

8. The bis(imino) compound of claim 7 wherein each of $R^3$-$R^5$ is hydrogen.

9. The bis(imino) compound of 8 wherein each of $R^1$ and $R^2$ is methyl.

10. An unsymmetric bis(imino) compound of the formula IV:

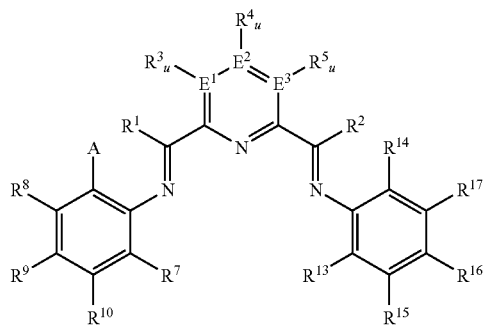

wherein:
- A is Cl;
- each of $R^1$ and $R^2$ is methyl;
- each of $R^3$-$R^5$ is hydrogen;
- each of $R^7$ and $R^9$ is methyl;
- each of $R^8$ and $R^{10}$, and $R^{15}$-$R^{17}$ is independently hydrogen, $C_1$-$C_{22}$-alkyl, $C_2$-$C_{22}$-alkenyl, $C_6$-$C_{22}$-aryl, arylalkyl having 1 to 10 carbon atoms in the alkyl radical and 6-20 carbon atoms in the aryl radical, $NR^{11}_2$, $OR^{11}$, halogen, $SiR^{12}_3$ or five-, six- or seven-membered heterocyclyl comprising at least one atom selected from the group consisting of N, P, O and S;
  - wherein $R^7$-$R^{10}$, and $R^{15}$-$R^{17}$ are optionally substituted by halogens, $NR^{11}_2$, $OR^{11}$ or $SiR^{12}_3$; and
  - wherein $R^7$ optionally bonds with $R^{10}$, $R^{10}$ optionally bonds with $R^9$, $R^9$ optionally bonds with $R^8$, $R^{17}$ optionally bonds with $R^{16}$, and $R^{16}$ optionally bonds with $R^{15}$, in each case to form a five-, six- or seven-membered carbocyclic or heterocyclic ring, the heterocyclic ring comprising at least one atom selected from the group consisting of N, P, O and S;
- each of $R^{13}$ and $R^{14}$ is independently a $C_1$-$C_3$-alkyl bonded with the aryl ring via a primary or secondary carbon atom;
- each $R^{11}$ is independently hydrogen, $C_1$-$C_{22}$-alkyl, $C_2$-$C_{22}$-alkenyl, $C_6$-$C_{22}$-aryl, arylalkyl having 1 to 10 carbon atoms in the alkyl radical and 6-20 carbon atoms in the aryl radical or $SiR^{12}_3$, wherein $R^{11}$ is optionally substituted by halogens and two $R^{11}$ radicals optionally bond to form a five- or six-membered ring;
- each $R^{12}$ is independently hydrogen, $C_1$-$C_{22}$-alkyl, $C_2$-$C_{22}$-alkenyl, $C_6$-$C_{22}$-aryl or arylalkyl having 1 to 10 carbon atoms in the alkyl radical and 6-20 carbon atoms in the aryl radical and two $R^{12}$ radicals optionally bond to form a five- or six-membered ring;
- each of $E^1$-$E^3$ is carbon; and
- each u is 1.

* * * * *